US011554254B2

(12) United States Patent
Pennell, II et al.

(10) Patent No.: US 11,554,254 B2
(45) Date of Patent: Jan. 17, 2023

(54) MEDICAL DEVICE ANCHOR

(71) Applicants: Infinivation Biomedical LLC, Moravia, NY (US); Bruce Kaufman, Wauwatosa, WI (US)

(72) Inventors: Thomas J. Pennell, II, Moravia, NY (US); Bruce Kaufman, Wauwatosa, WI (US)

(73) Assignee: Infinivation Biomedical LLC, Moravia, NY (US)

( * ) Notice: Subject to any disclaimer, the term of this patent is extended or adjusted under 35 U.S.C. 154(b) by 0 days.

(21) Appl. No.: 16/856,235

(22) Filed: Apr. 23, 2020

(65) Prior Publication Data

US 2021/0060301 A1 Mar. 4, 2021

Related U.S. Application Data

(60) Provisional application No. 62/892,859, filed on Aug. 28, 2019.

(51) Int. Cl.
*A61M 25/02* (2006.01)

(52) U.S. Cl.
CPC ....... *A61M 25/02* (2013.01); *A61M 2025/024* (2013.01); *A61M 2025/028* (2013.01); *A61M 2025/0246* (2013.01)

(58) Field of Classification Search
CPC ............ A61M 25/02; A61M 2025/028; A61M 2025/0246; A61M 2025/0233; A61M 2039/222; A61M 39/221; A61M 2025/024; A61M 2025/0206; A61J 15/0061; A61J 15/0026; A61J 15/0065
See application file for complete search history.

(56) References Cited

U.S. PATENT DOCUMENTS

| 2,727,512 | A | * | 12/1955 | Muller | ........... | A61M 25/02 |
| | | | | | | 128/DIG. 26 |
| 4,029,103 | A | * | 6/1977 | McConnell | ........ | A61M 25/02 |
| | | | | | | 604/179 |
| 4,493,134 | A | * | 1/1985 | Karr | ............. | H01R 4/00 |
| | | | | | | 439/456 |

(Continued)

OTHER PUBLICATIONS

U.S. Patent & Trademark Office (ISA/US), International Search Report and Written Opinion of the International Searching Authority from International Patent Application No. PCT/US20/29525, completed Jun. 9, 2020 and dated Jul. 16, 2020.

*Primary Examiner* — Theodore J Stigell
(74) *Attorney, Agent, or Firm* — Timothy W. Menasco, Esq.; Harter Secrest & Emery LLP

(57) ABSTRACT

Embodiments of the present disclosure provide a method and apparatus for securing a medical device. An exemplary apparatus includes a body having an inner portion and an edge portion, the edge portion defining a terminal end of the body, the body defining at least one surface spanning the inner portion and the edge portion. The apparatus further includes at least one wing fixedly coupled to the edge portion of the body, the at least one wing defining at least one hole extending through the at least one wing. The apparatus still further includes at least one channel disposed on the at least one surface of the body, the at least one channel having a first terminal end at the edge portion of the body, wherein the at least one channel comprises at least one curve.

15 Claims, 25 Drawing Sheets

(56) References Cited

U.S. PATENT DOCUMENTS

| | | | | |
|---|---|---|---|---|
| 5,643,217 | A | * | 7/1997 | Dobkin ................. A61B 17/00 |
| | | | | 604/174 |
| 8,584,323 | B2 | * | 11/2013 | Pang .................... F16G 11/048 |
| | | | | 24/132 R |
| 2003/0199831 | A1 | | 10/2003 | Morris et al. |
| 2004/0204685 | A1 | * | 10/2004 | Wright ................... A61M 5/32 |
| | | | | 604/174 |
| 2005/0015128 | A1 | * | 1/2005 | Rezai ................. A61N 1/0539 |
| | | | | 607/115 |
| 2005/0054985 | A1 | * | 3/2005 | Mogg .................. A61M 25/02 |
| | | | | 604/174 |
| 2012/0184915 | A1 | | 7/2012 | Bierman et al. |
| 2012/0245529 | A1 | * | 9/2012 | Hummen ............. A61N 1/0539 |
| | | | | 604/175 |
| 2013/0345639 | A1 | | 12/2013 | Spitter |
| 2014/0343501 | A1 | | 11/2014 | Bierman et al. |
| 2017/0216556 | A1 | | 8/2017 | Bierman et al. |
| 2019/0091446 | A1 | * | 3/2019 | Hartmann ......... A61M 5/14248 |

* cited by examiner

MEDICAL DEVICE ANCHOR

BACKGROUND OF THE INVENTION

Field of the Invention

Embodiments of the present disclosure present a method and apparatus for medical procedures. Embodiments of the present disclosure present in particularity a method and apparatus for securing a medical device to a patient.

Description of Related Art

Modern medical care has become dependent on the use of various medical devices such as catheters and "leads" that are implanted or inserted into the body of a patient. There are catheters that are used to remove substances from the body and deliver substances into the body, such as medications or fluids.

Regardless of the type of catheter or lead, both medical devices are required to remain in a fixed position for some amount of time in order to properly perform their function. The amount of deviation from an initial position that provides adequate function of the medical device can vary from fractions of a millimeter to several centimeters depending on the type of function and location of the medical device. Deviated movement can lead to complete loss of function, inappropriate function, or decreased function for the medical device. The result of such deviated movement can range from being innocuous to inconvenient, requiring time and resources to re-establish the original position or replace the medical device in its entirety. Misalignment or deviation of the medical device from its original position may become an immediate life or death threatening event, especially if the medical device fails to perform or deliver treatment to the wrong location on the patient. Unfortunately, movement of these medical devices is a frequent problem in the health care industry.

To prevent unwanted medical device movement, there is usually some method of securing or anchoring the medical devices to or within the patient. The type and method of anchoring will vary depending on the medical device's sensitivity to movement and position and whether the medical device is implanted completely within the body or it is externalized from the body of the patient. The method of securing the medical device is also of importance. Any method of securing a catheter or lead needs to connect that catheter or lead to the patient's body tissue. The anchoring method must be attached to the body to prevent movement. In addition, the catheter or lead may not be allowed to move through the securing anchor in order to prevent deviation. Finally, the function of the medical device must not be impaired by the method of anchoring (e.g., preventing flow through a catheter or interfering with a signal through a lead).

Securing the medical device also takes into consideration the amount of motion that can be tolerated by the medical device (e.g., sub-millimeter vs centimeter) and the types of movement that may be encountered by the medical device (e.g., patient movement in the environment and relative movement of tissue within the patient).

Critical care medicine is dependent on the use of venous catheters to continuously deliver medication. These catheters are usually externalized through the skin and are thus subject to different types of dislocation events. Although movement tolerances can be greater than with cerebrospinal fluid (CSF) diversion, it still remains critical to secure the lines from movement and to maintain that location over long periods of time.

BRIEF SUMMARY OF THE INVENTION

In view of the foregoing, it is an object of the present disclosure to provide a method and apparatus for securing a medical device to a patient.

A first exemplary embodiment of the present disclosure provides an apparatus for medical procedures. The apparatus includes a body having an inner portion and an edge portion, the edge portion defining a terminal end of the body, the body defining at least one surface spanning the inner portion and the edge portion. The apparatus further includes at least one wing fixedly coupled to the edge portion of the body, the at least one wing defining at least one hole extending through the at least one wing. The apparatus still further includes at least one channel disposed on the at least one surface of the body, the at least one channel having a first terminal end at the edge portion of the body, wherein the at least one channel comprises at least one curve.

A second exemplary embodiment of the present disclosure provides a method of forming. The method includes forming a body having an inner portion and an edge portion, the edge portion defining a terminal boundary of the body, the body defining at least one surface spanning the inner portion and the edge portion. The method further includes forming at least one wing fixedly coupled to the edge portion of the body, the at least one wing defining at least one hole extending through the at least one wing. The method still further includes forming at least one channel disposed on the at least one surface of the body, the at least one channel having a first terminal end at the edge portion of the body, wherein the at least one channel comprises at least one curve.

A third exemplary embodiment of the present disclosure provides an apparatus for medical procedures. The apparatus includes a body having an inner portion and an edge portion, the edge portion defining a terminal end of the body, the body defining at least one surface spanning the inner portion and the edge portion. The apparatus further includes at least one channel disposed on the at least one surface of the body, the at least one channel having a first terminal end at the edge portion of the body, wherein the at least one channel comprises at least one curve. The apparatus still further includes at least one opening disposed on the at least one surface of the body, wherein the at least one opening is in coextensive with the at least one channel.

The following will describe embodiments of the present disclosure, but it should be appreciated that the present disclosure is not limited to the described embodiments and various modifications of the invention are possible without departing from the basic principles. The scope of the present disclosure is therefore to be determined solely by the appended claims.

DETAILED DESCRIPTION OF THE INVENTION

Figure 1:
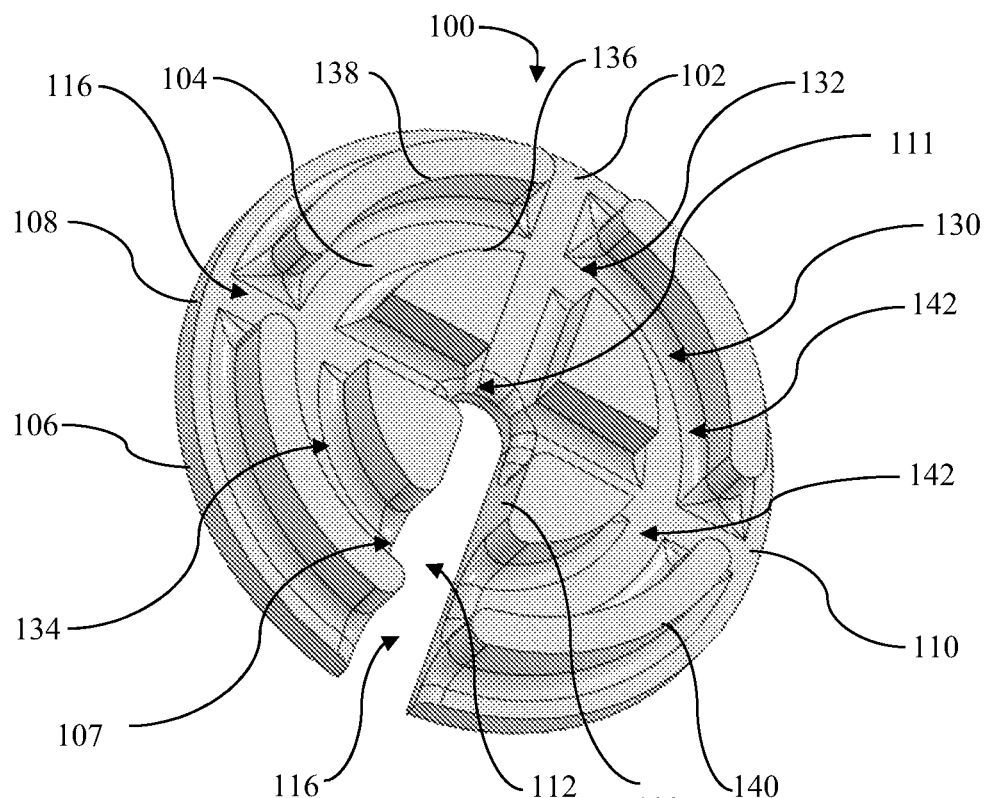
FIG. 1 is a top perspective view of a first embodiment of a medical device anchor of the present disclosure.
Figure 2:
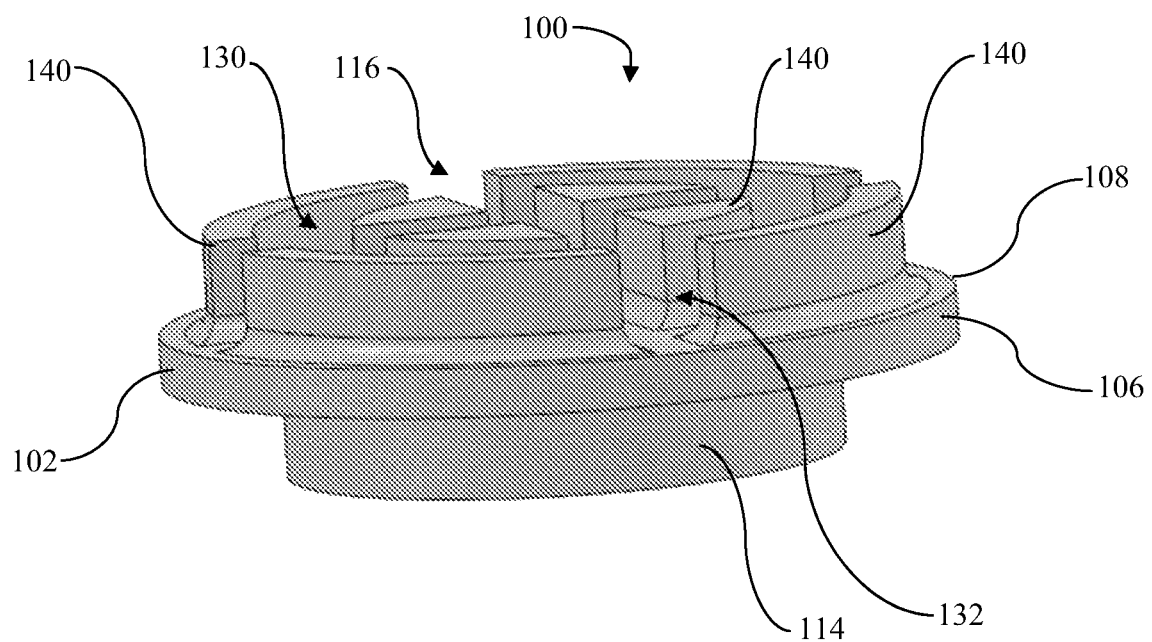
FIG. 2 is a side perspective view of the medical device anchor of FIG. 1 of the present disclosure.
Figure 3:
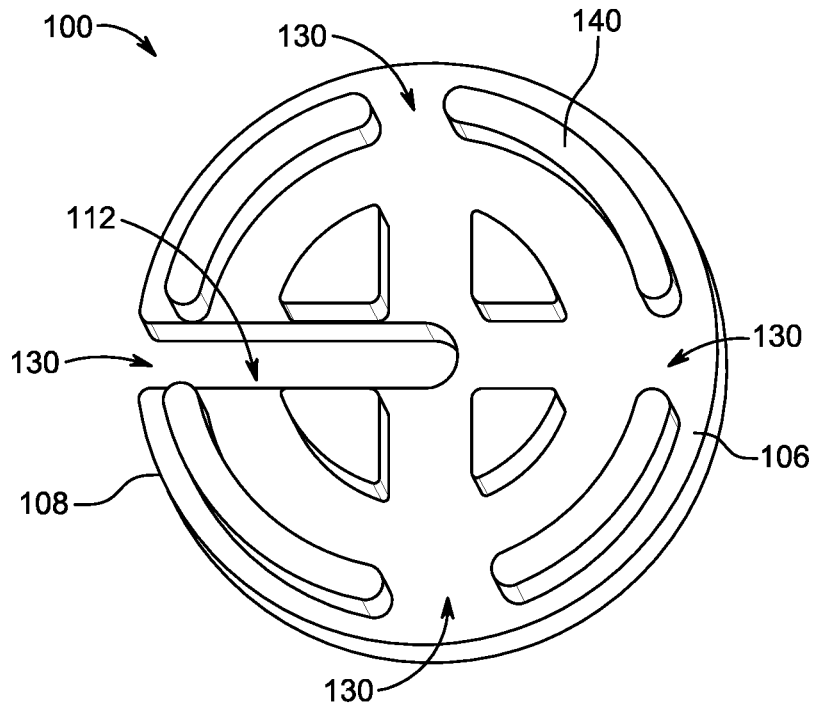
FIG. 3 is a top elevational view of the medical device anchor of FIG. 1 of the present disclosure.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

The detailed description set forth below is intended as a description of various configurations of the present invention and is not intended to represent the only configurations in which the present invention may be practiced. It will be apparent, however, to those of ordinary skill in the art that the present invention is not limited to the specific details set forth herein and may be practiced without these specific details.

Embodiments of the present disclosure provide a method and apparatus operable to secure a medical device (e.g., catheters and "leads") to a patient or user to inhibit dislodgement or repositioning of the medical device from a first position while not impairing the function of the medical device (e.g., preventing flow through a catheter or interfering with a signal through a lead). Embodiments of the present disclosure may also be suitable for both implantable and non-implantable applications including transcutaneous catheters that can hold a catheter's proximal tip in position relative to the catheter's entry point into the body. In Neurosurgery, the medical device anchor can be used to hold a ventricular catheter tip position in the ventricles relative to the medical device anchor. Embodiments of the present disclosure may further not have a medical device passing over and under itself. Embodiments of the present disclosure may yet further consist of a multi-piece medical device anchor that may be used as a single component, allowing for better securement of catheters against migration. Examples of catheters include intravenous or intra-arterial catheters (e.g., peripheral or central, venous, or arterial), drug delivery catheters (e.g., those that are connected to external or internal sources), or enteral feeding tubes. Other catheters are used to remove fluids or substances such as gastrointestinal drainage catheters (e.g., stomach, small bowel, and gallbladder), urinary catheters (e.g., from the bladder or ureter), or cerebrospinal fluid catheters (e.g., brain and spine). Moreover, there are a number of "leads" that can be electrodes or sensor-related cables and fibers that can deliver a signal (e.g., electrical, mechanical, and/or chemical) to a particular body region or used to retrieve such signals from the body of a patient.

Figure 4:
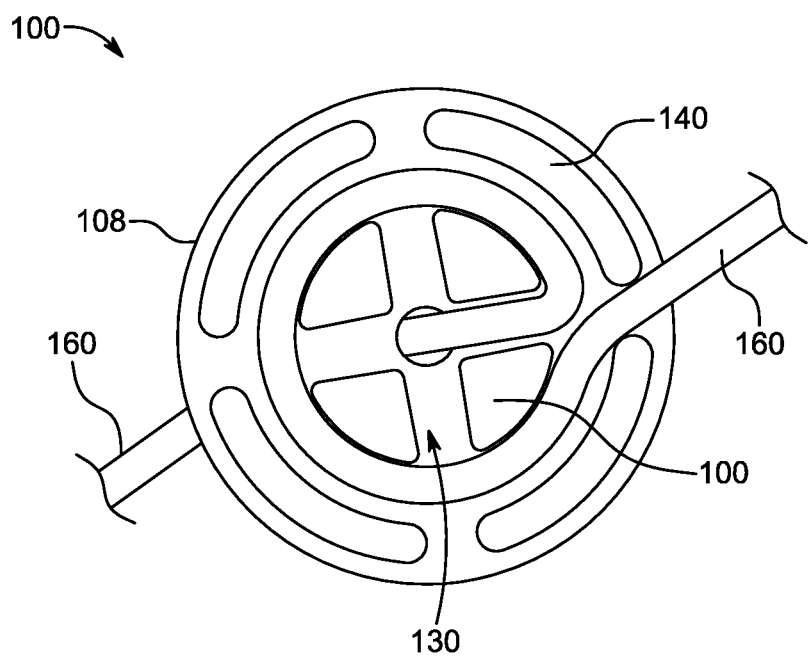
FIG. 4 is a top elevational view of the medical device anchor of FIG. 1 of the present disclosure along with a medical device.

Referring to FIGS. 1-7 and 16, shown are perspective and elevational views of an exemplary medical device anchor operable for performing exemplary embodiments of the present disclosure such as securing a medical device 160 (e.g., catheters, "leads," and tubes). Shown in FIGS. 1-7 and 16 is a device anchor 100 having a body 102 with an inner portion 104 and an edge portion 106. The edge portion 106 of the body 102 includes a terminal end 108. Embodiments include the body 102 of the device anchor 100 as having a surface 110, a hole 112, and a bottom portion 114. Embodiments include the hole 112 of the body 102 as an extended hole/elongated notch as shown in FIGS. 1 and 26-28, and as a circular hole as shown in FIG. 4. The embodiment of hole 112 illustrated in FIG. 1 shows an elongated notch that extends from the radial edge portion 106 to the radial center of the body 102. The elongated notch 112 shown in FIG. 1 is defined by a first body edge 107 a spaced apart second body edge 109, and a curved body edge 111. The first body edge 107 is coupled to curved body edge 111 which is coupled to the second body edge 109. First body edge 107 in one embodiment is parallel to the second body edge 109. In another embodiment first body edge 107 and second body edge 109 is not parallel to one another. It should be appreciated that curved body edge 111 can be located at the radial center of body 102 in one embodiment, but can be located adjacent to or spaced from the radial center of the body 102. First body edge 107 extends from the edge portion 106 to the curved body edge 107 located either at the radial center of body 102 or adjacent to the radial center of body 102. Second body edge 111 is radially spaced apart from first body edge 107 and extends from the edge portion 106 to the curved body edge 107 located either at the radial center of body 102 or adjacent to the radial center of body 102.

Also, as shown in FIGS. 1-7 and 16, embodiments of the device anchor 100 include a plurality of walls 140 that form spaces 142 between the adjacent walls 140. Embodiments of the present disclosure include the spaces 142 between the walls 140 forming a plurality of channels 130. Embodiments of the present disclosure include the channels 130 being sized to accommodate the medical device 160. Each of the plurality of channels 130 include terminals ends 132 and a curve 134 that are configured to increase the surface friction between the walls 140 and the medical device 160 such that the implanted part of the medical device 160 remains fixed in its position even when the external part of the medical device 160 is suddenly pulled. In other words, the curvature of the channels 130 combined with the surface of the walls 140 along the channels 130 create surface friction with a device (e.g., a catheter) that is placed within the channels 130, which opposes the movement or slipping of the catheter through channels 130.

Figure 5:
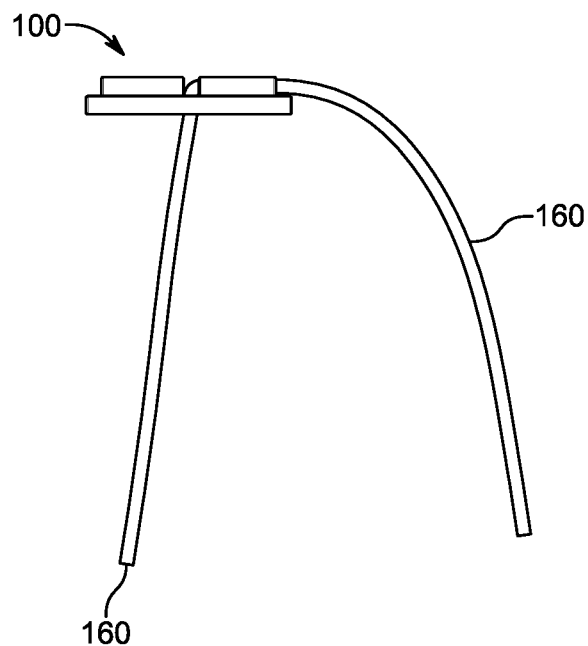
FIG. 5 is side elevational view of the medical device anchor of FIG. 4 of the present disclosure along with the medical device.
Figure 6:
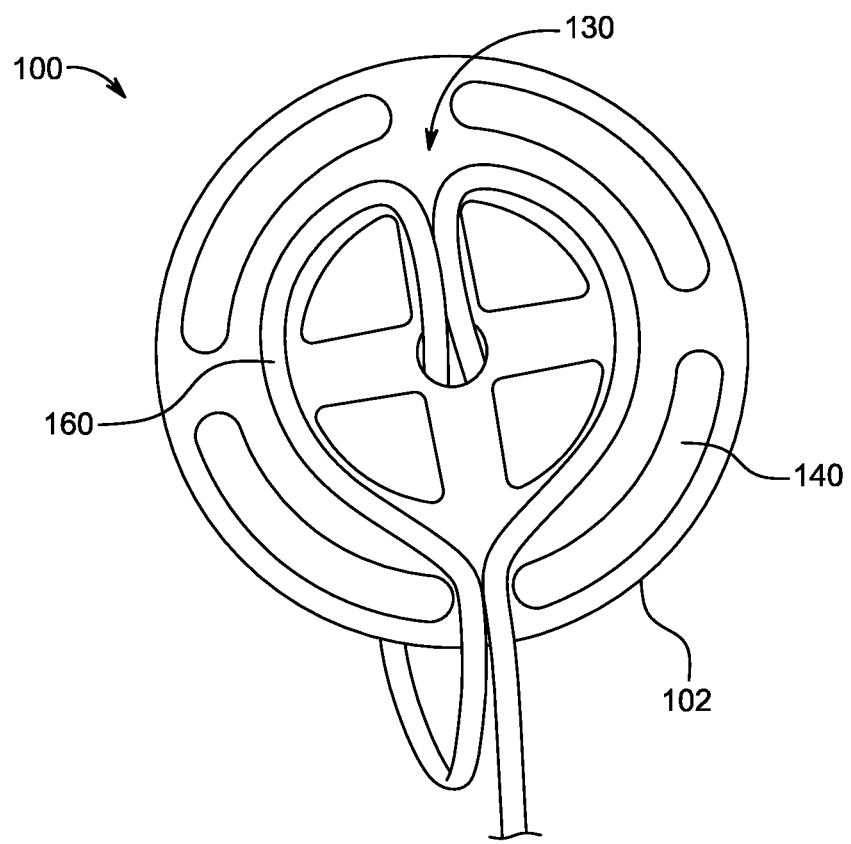
FIG. 6 is a top elevational view of the medical device anchor of FIG. 1 of the present disclosure along with a plurality of medical devices.

Embodiments of the present disclosure include the medical device 160 entering the body 102 of the device anchor 100 and being directed into a horizontal internal rotational channel 130 defined by an internal radial barrier 136 and an external radial barrier 138 of the walls 140. The channel 130 serves to increase the amount of surface area that contacts the medical device 160. By passing the medical device 160 through a tortuous path by way of the channels 130, embodiments include increased friction between the medical device 160 and device anchor 100, resulting in limiting or eliminating the ability of the medical device 160 to move or be repositioned from its intended/initial position. It should be appreciated that while FIGS. 5 and 6 illustrate a medical device 160 (e.g. a catheter as shown) that passes through a hole 112, embodiments include medical device 160 not passing through hole 112. Embodiments include catheter 160 passing exclusively through channels 130 and not hole 112 such that enough surface friction is created between the catheter 160 and walls 140 that catheter 160 does not move or substantially prevents movement of catheter 160 through channels 130.

The interior barrier 136 of the channel 130 is formed by any number of walls/pegs 140 (e.g., 4 pegs) of which the outer surface of the pegs forms the interior barrier 136 of the channel 130. The outer barrier 138 of the channel 130 is formed by any number of walls/elongated surfaces 140 (e.g., 4 elongated surfaces) of which the inner surface of the elongated surfaces forms the exterior barrier 138 of the channel 130. Embodiments include profile shapes of the internal rotational channel 130 be square, rounded, "V" shaped, or any other shape suitable for the intended purpose to maximize friction against the exterior surface of the medical device 160.

In another embodiment of the present disclosure, inserts (not shown) may be constructed and positioned accordingly to allow medical devices 160 of various sizes to be used with the device anchor 100. Embodiments of the present disclosure include ventricular shunt catheters with an approximately ⅛" outer diameter (OD. In this embodiment, the insert pieces may be injection molded to fit within the ⅛" OD channel, with a 1/16" channel 130 molded into the same. Embodiments also include one insert being pressed into the channel 130, the 1/16" medical device 160 is inserted, and yet another insert can be added from above creating a "sandwich" with the medical device 160 in the middle. Embodiments include a cap 150 that is configured to enclose the medical device 160 within the device anchor 100, as further described below.

In further embodiments, the body 102 of the device anchor 100 includes a plurality of inlets and outlets 116 to allow for entry and exit of the medical device 160. This allows the medical device 160 to enter the device anchor 100 at different angles. Embodiment include the device anchor 100 having four lateral openings 116 and one vertical opening 112 from below the device anchor 100.

In embodiments of the present disclosure, the medical device 160 enters at an acute angle corner through the inlet 116 along a tight radius (e.g., between 3/16$^{th}$ circle radius to 90 degrees) to enter the channel 130. When tension is applied to the medical device 160 that is wound about a tight radius, fluid flow through a lumen can be stopped or an internal electrode signal conduction may be damaged. To reduce the potential for damage to the medical device 160 the radius of the entry corner may be increased accordingly.

Embodiments of the present disclosure include the medical device 160 being introduced into the body 102 of the device anchor 100 from underneath the device anchor 100. Embodiments include the medical device 160 being bent over a turn (shown in FIGS. 4 and 5 as a 90 degree turn) and then entering a horizontal internal channel 130. Embodiments include the medical device 160 entering the device anchor 100 from below and may be deflected by the turn as shown in FIG. 5.

Further embodiments include the device anchor 100 including a hollow cylindrical-shape bottom portion 114 beneath the body 102 of the device anchor 100. The bottom portion 114 can be a downwardly extending circular wall sized to have a radius less than the radius of the body 102. Embodiments of bottom portion 114 are operable to be implanted within a patient (e.g., in a hole in the skull of the patient) to aid in obstructing lateral movement of the device anchor 100. The bottom portion 114 of the body 102 may include inlets and outlets (not shown) to allow entry and exit of the medical device 160. Other embodiments include wall-like protrusions projecting downwardly from the bottom portion 114 of the body 102. The bottom portion 114 of the device anchor 100 adds structure that serves as a directional guide path for the medical device 160, as well as additional securement of the medical device 160 to the device anchor 100. In addition, such a cylindrical bottom portion 114 underneath the body 102 of the device anchor 100 also assists in preventing lateral motion of the body 102 in tissue of the patient. The additional vertical segment of the bottom portion 114 of the device anchor 100 also separates components of the device anchor 100 or is integrated wholly into the body 102 of the device anchor 100. Additional structures, components, extensions, and protrusions may be incorporated into or connected to the device anchor 100 depending on the medical device 160 directionality requirements.

Further embodiments of the present disclosure include having an elongated notch 112 beginning at one of the inlets/outlets 116 and ending towards the center of the device anchor 100 to allow for placement of the device anchor 100 onto an existing medical device (i.e., already placed) without disturbing the medical device's 160 initial placement on the patient.

Embodiments of the device anchor 100 include "suture loops," which are integral holes within or to the sides of the medical device 160 that can be used to secure the medical device 160 to the patient with sutures, ties, or other methods of attachment such as small screws to firm tissues. Further embodiments include an array of suture loop holes that form through each or some of the base pegs/wings 120. The body 102 of the device anchor 100 may further include separate loops or wings along the edge portion 106 of the device anchor 100. This allows the sutures/ties to hold the medical device 160 within the device anchor's 100 channels 130 and does not require use of a cap or lid 150.

Further embodiments of the device anchor 100 also utilize an adhesive on the underside of the body 102 of the device anchor 100 to secure the device anchor 100 to the skin or other body surface of the patient. In the embodiment depicted in FIG. 23, the bottom region of the body 102 may also include an adhesive to secure the device anchor 100 to the patient. The adhesive may be glue, a tacky substance, paste, cyanoacrylate glue, or any other adhesive suitable for the intended purpose and understood by a person of ordinary skill in the art.

Embodiments of the present disclosure include the device anchor 100 securing more than one medical device 160 at the same time with one body 102 and cap 150 assembly. Two medical devices 160 can be installed into the same channel 130 of the device anchor 100. For example, the two medical devices 160 can be folded into the same channel 130 in opposite directions with respect to each other as shown in FIG. 6. Alternatively, the body 102 of the device anchor 100 may be constructed with multiple concentric internal channels 130 to secure a plurality of medical devices 160.

Embodiments of the present disclosure include the inlets 116, the outlets 116, and the channels 130 including dimensions that may be altered to better secure medical devices 160 having different shapes and sizes. Embodiments include device anchors 100 having custom fitted bodies 102 to the patient, custom fitted channels 130 to corresponding medical devices 160, or insert structures that are used in conjunction with a single body 102 of the device anchor 100 that holds multiple sized medical devices 160.

Embodiments of the present disclosure include the device anchor 100 having components that are designed to be minimal in size (e.g., both diameter and height) in order to limit tissue stress. Embodiments include the underside of the body 102 of the device anchor 100 being curved to better mate the device anchor 100 with a curved surface (e.g., a surface of a skull of the patient). The body 102 and the channels 130 of the device anchor 100 also may be sized accordingly depending on the cross-section, size, length, and thickness of the medical devices 160 secured by the device anchor 100. For example, smaller or larger channels 130 and larger or smaller radii of curvature of the channels 130 to compliment smaller or larger medical device 160 diameters. Embodiments of the present disclosure include the device anchor 100 being stackable on top of another device anchor 100 such that multiple medical devices 160 are utilized at the same time.

Further embodiments of the present disclosure include the device anchor 100 as being made by high volume injection molding. However, the device anchor 100 also may be made by additive manufacturing, casting, or any other method suitable for the intended purpose and understood by a person of ordinary skill in the art. Embodiments include the device anchor 100 and the cap 150 being made of biocompatible materials. For example, silicone/silastic device anchors 100 provide the most surface friction presuming that many medical devices 160 are also constructed of silicone or silastic. Other materials include polyurethane, high density polyethylene (HDPE), or Teflon (PTFE) that are suitable for implantation. However, selection of which material to use may be based on surface properties as PTFE may be too "slippery" to provide adequate friction against the catheter 160. Polycarbonate or acrylic are also plastics that can be used to make the device anchor 100, which allows clinicians to see the status of the catheter 160 given that the catheter 160 is non-opaque.

Titanium or stainless steel are metals that are suitable for implantation. Titanium has the potential for osseointegration that is advantageous when such incorporation is desired, but this can make removal difficult in the future.

Embodiments include the device anchor 100 being constructed with rigid materials, flexible materials, or a combination of both. A soft, flexible base material may be useful for interfacing with skin for improved patient comfort. A soft exterior coating also prevents tissue injury in implanted applications. The body 102 of the device anchor 100 may be curved or constructed of a material that will conform to the curved tissue surfaces of the patient underneath the base. Examples include silicone, polycarbonate, or another soft material suitable for the intended purpose and understood by a person of ordinary skill in the art.

Embodiments of the present disclosure include the device anchor 100 having surface properties based on material that is selected to maximize the coefficient of friction between the medical device 160 and the device anchor 100. The surface design of the device anchor 100 may also be modified (e.g., smoothed, roughened, or coated with another material) to maximize the coefficient of friction between the medical device 160 and the device anchor 100. In embodiments where the surface of the device anchor 100 is roughened, the exterior surface of the medical device 160 may not be abraded by the roughened surface of the device anchor 100.

Embodiments of the present disclosure include the medical device 160 being secured to the device anchor 100 in addition to the tension created by the channels 130 and the walls 140 of the device anchor 100 without the cap 150. For example, the medical device 160 may be further secured to the device anchor 100 with sutures, adhesives, staples, glue, tape, or any other method of securement suitable for the intended purpose and understood by a person of ordinary skill in the art.

Embodiments of the present disclosure include the device anchor being a "reservoir" for additional sections of the medical device 160. For example, a surgeon may suddenly require additional catheter length to an existing catheter 160 already in position. By having extra catheter material 160 spooled or wrapped into the device anchor 100, catheter length can be withdrawn from the device anchor 160 and utilized accordingly.

Figure 16:
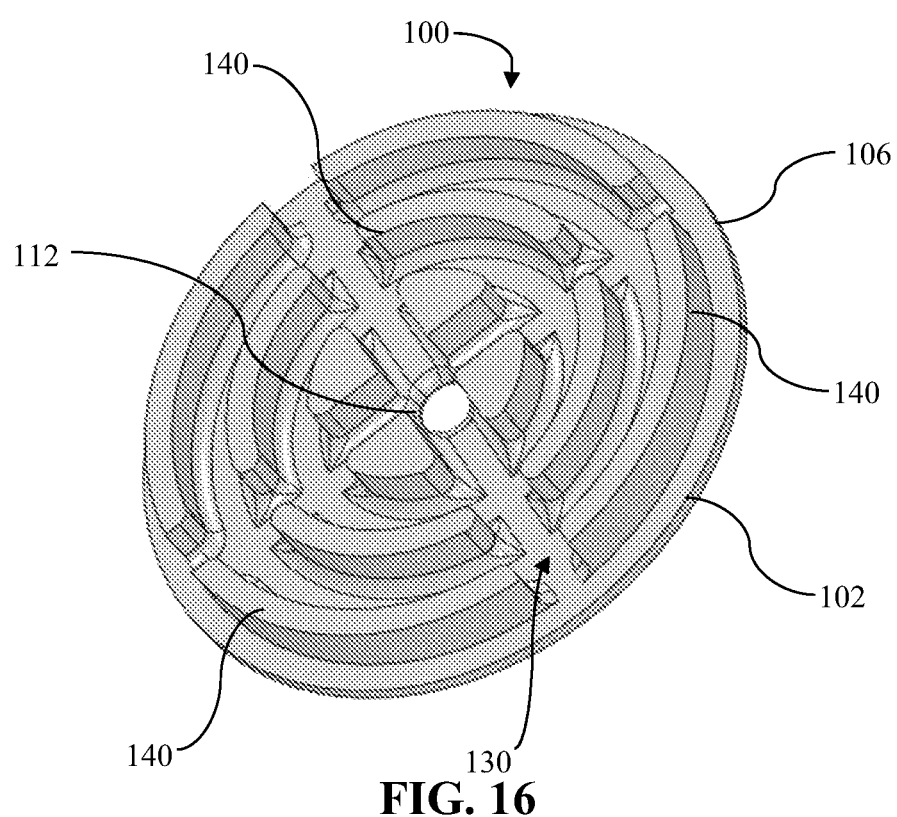
FIG. 16 is a top perspective view of the medical device anchor of FIG. 1 of the present disclosure with an additional set of walls.

Embodiments of the present disclosure include additional sets of walls 140 and channels 130 as shown in FIG. 16. The additional sets of walls 140 and channels 130 may act as a medical device 160 storage, such as catheter storage. Embodiments include about 2.25 inches of medical device 160 storage that also may be used as an extension for the medical device 160.

Figure 7:
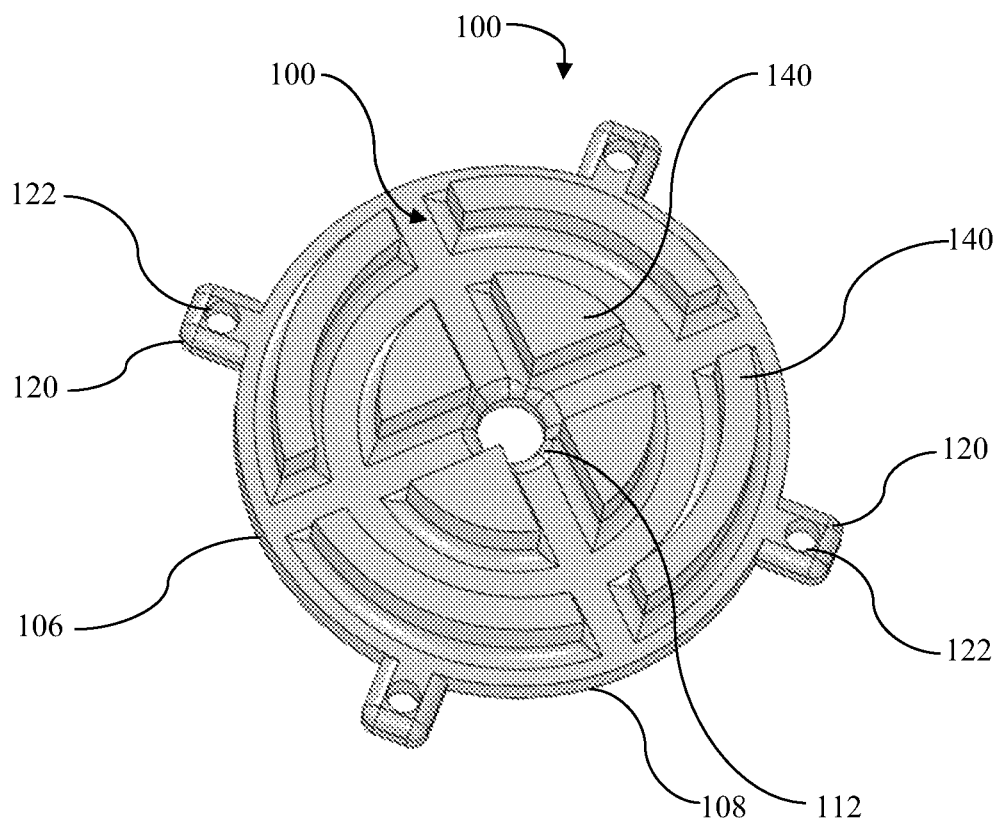
FIG. 7 is a top perspective view of the medical device anchor of FIG. 1 of the present disclosure along with a plurality of wings.

As shown in FIG. 7, embodiments of the present disclosure include the body 102 of the device anchor 100 as having a plurality of wings 120 that are coupled to the body 102 of the device anchor 100. Embodiments include the wings 120 and the body 102 of the device anchor 100 as being one homogenous piece. Other embodiments include the wings 120 as being separable from the body 102 of the device anchor 100. The wings 120 of the anchor device 100 also include a hole 122 that may be utilized to secure the device anchor 100 to a patient. The wings 120 are illustrated as square-like in FIG. 7, however, other polygonal shapes are envisioned that are suitable for the intended purpose and understood by a person of ordinary skill in the art.

Figure 22:
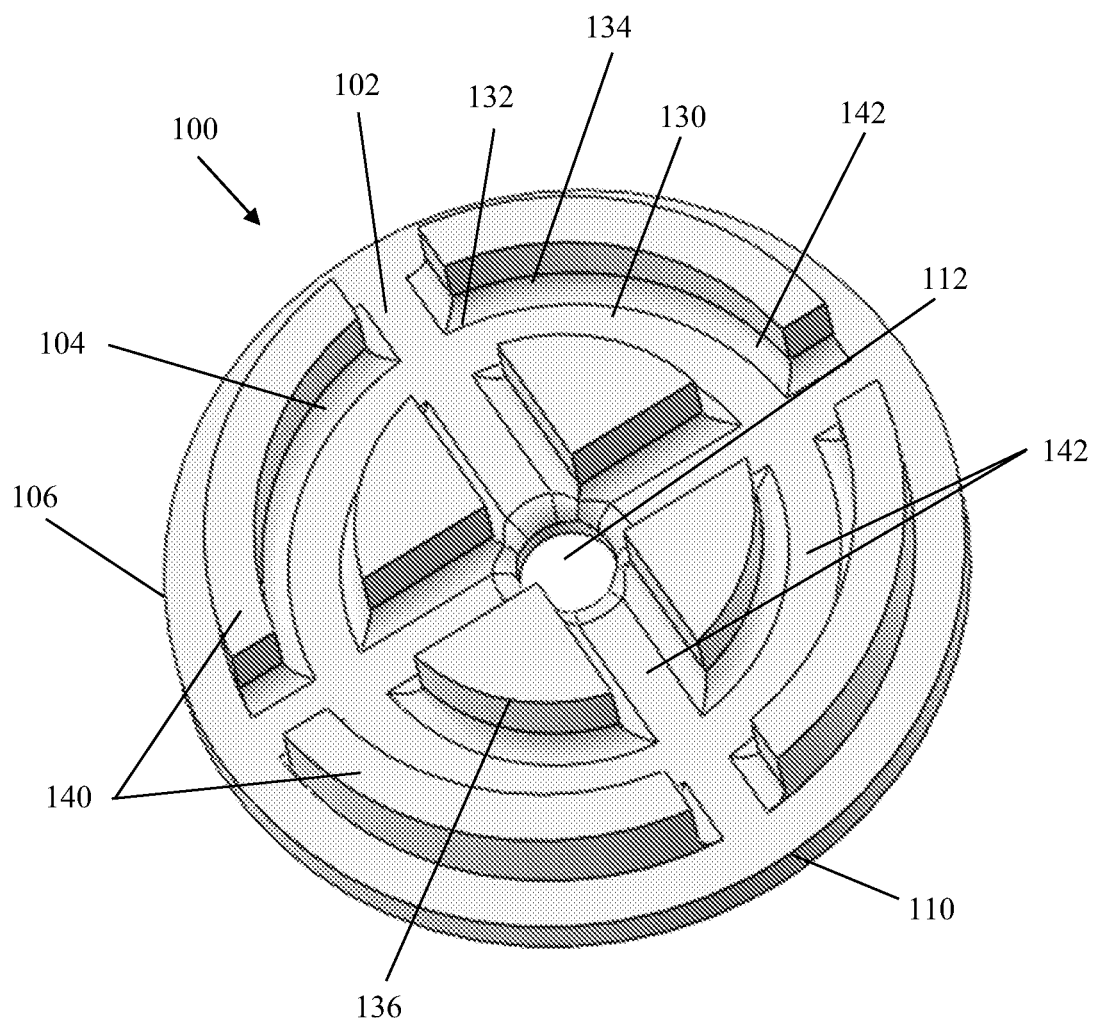
FIG. 22 is a top view of another embodiment of the medical device anchor suitable for use in practicing exemplary embodiments of the present disclosure.
Figure 23:
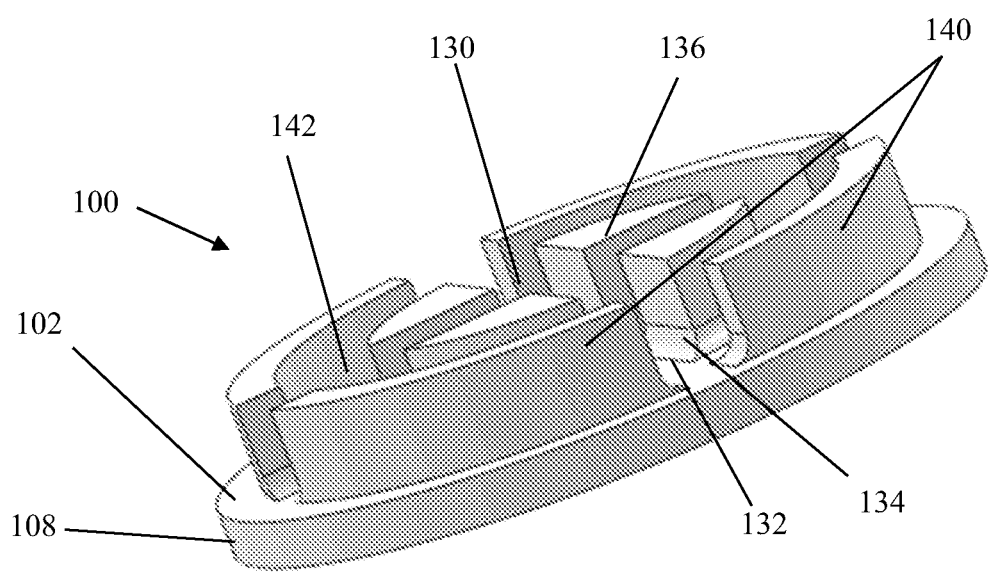
FIG. 23 is a side view of the medical device anchor suitable for use in practicing exemplary embodiments of the present disclosure.
Figure 24:
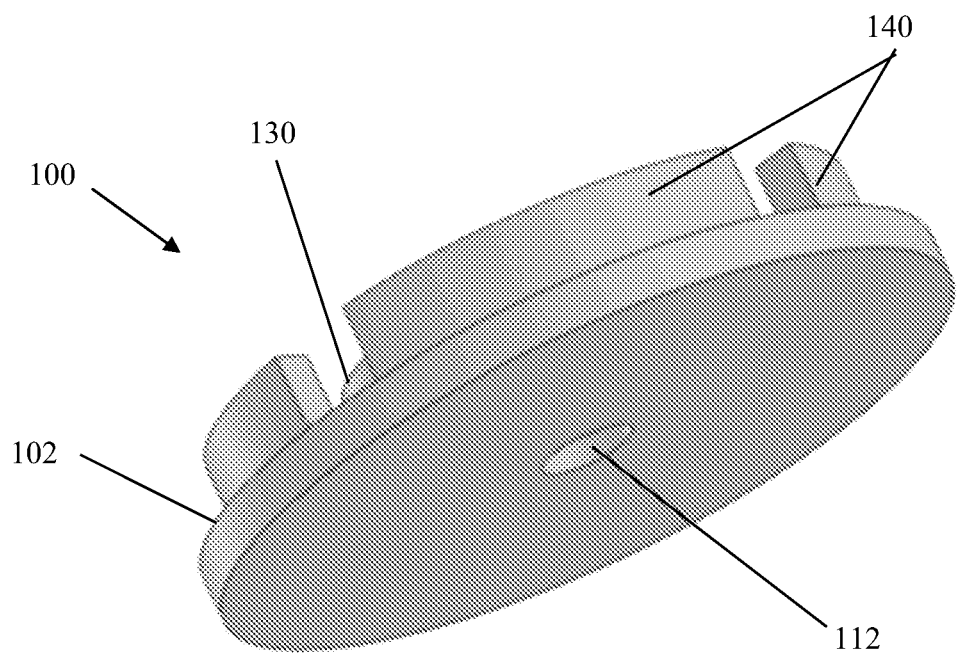
FIG. 24 is a bottom perspective view of the medical device anchor suitable for use in practicing exemplary embodiments of the present disclosure.
Figure 25:
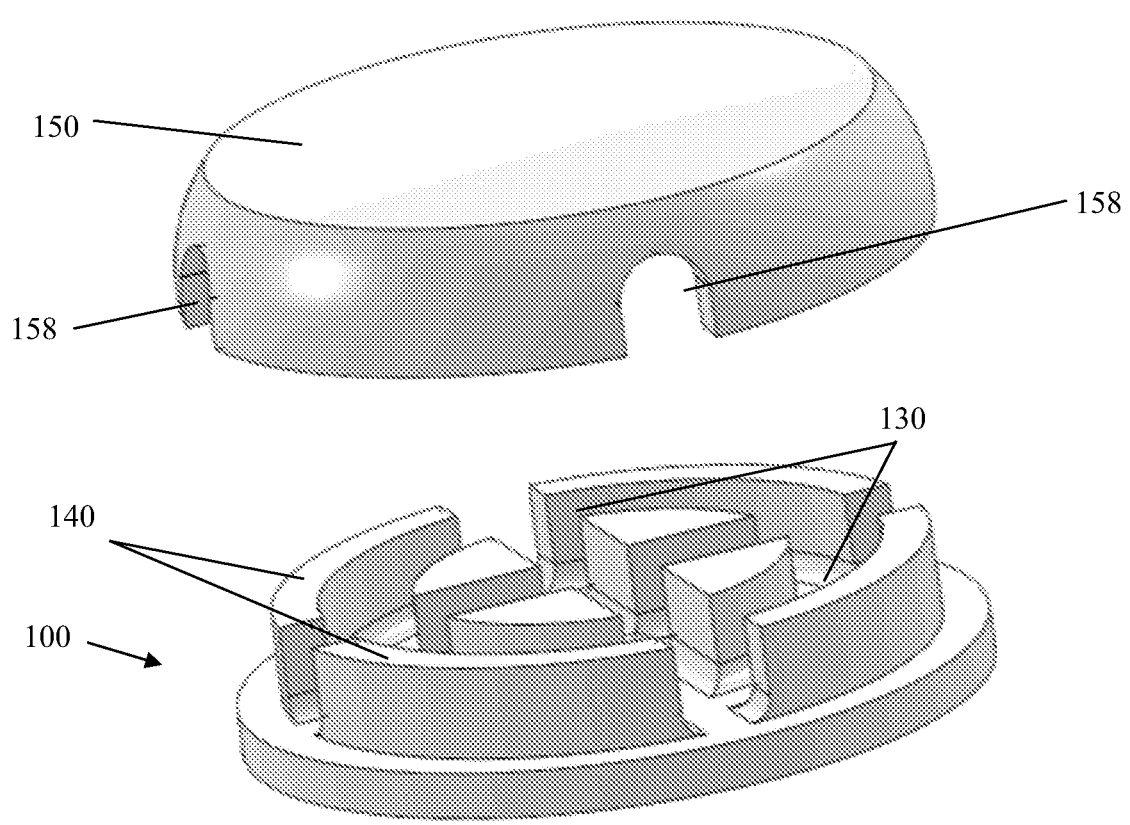
FIG. 25 is a side perspective view of the medical device anchor and a cap suitable for use in practicing exemplary embodiments of the present disclosure.
Figure 26:
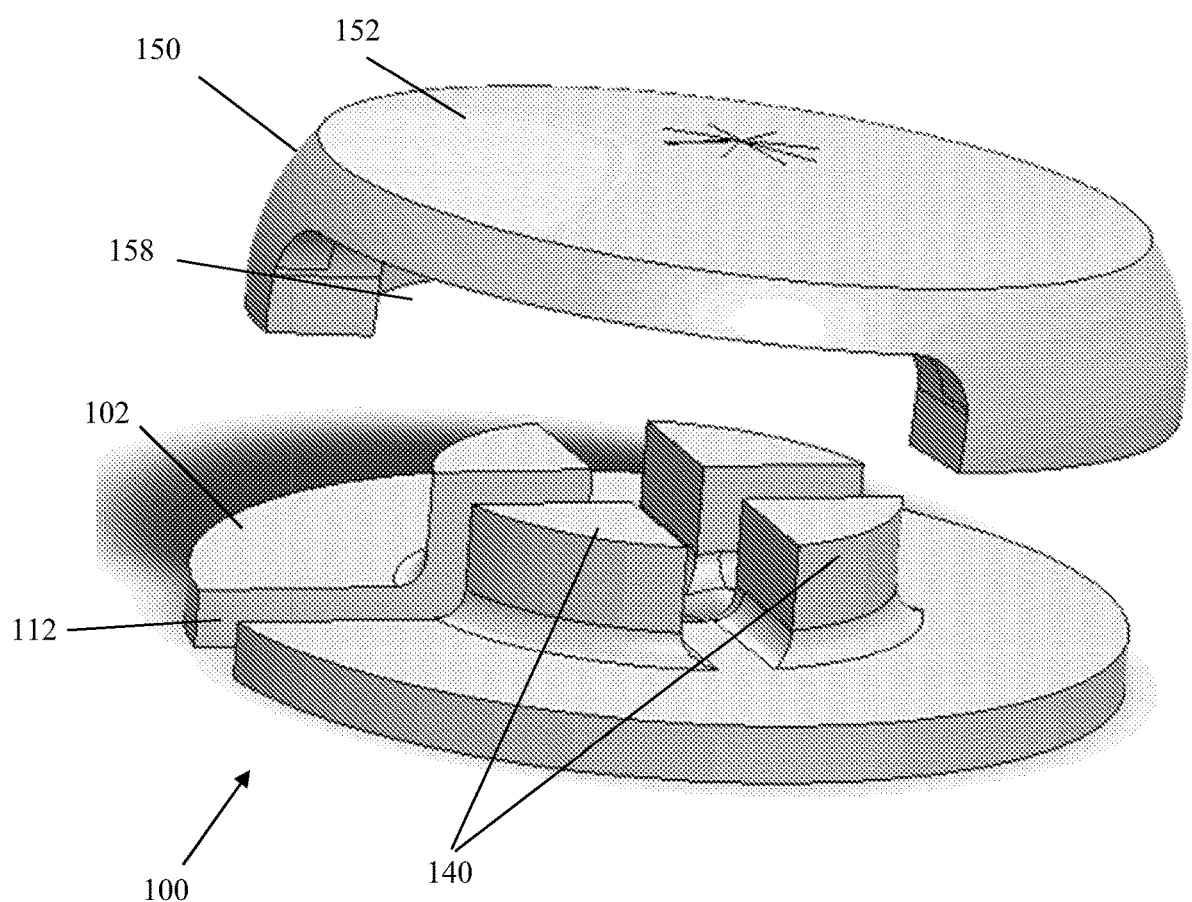
FIG. 26 is a side perspective view of yet another medical device anchor suitable for use in practicing exemplary embodiments of the present disclosure.
Figure 27:
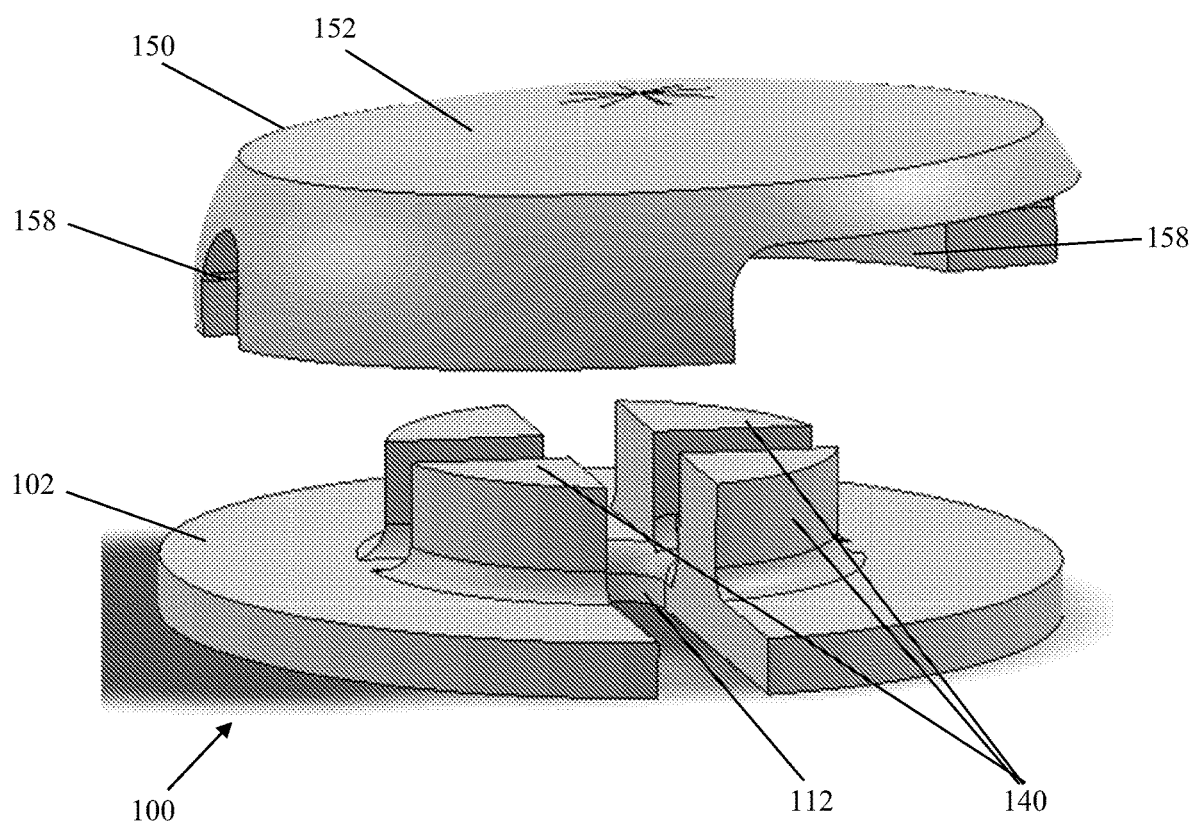
FIG. 27 is another side perspective view of the medical device anchor and cap suitable for use in practicing exemplary embodiments of the present disclosure.
Figure 28:
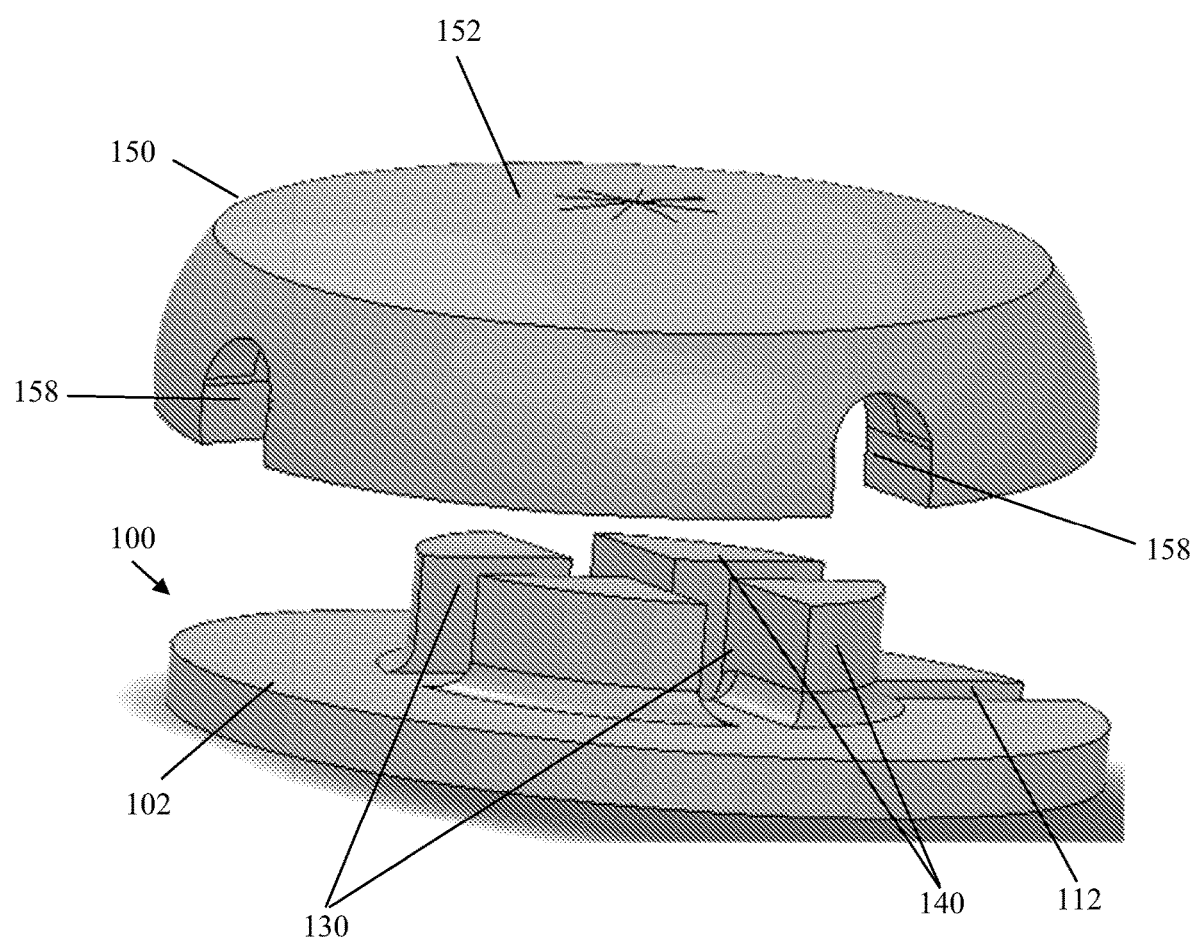
FIG. 28 is yet another side perspective view of the medical device anchor and cap suitable for use in practicing exemplary embodiments of the present disclosure.
Figure 29:
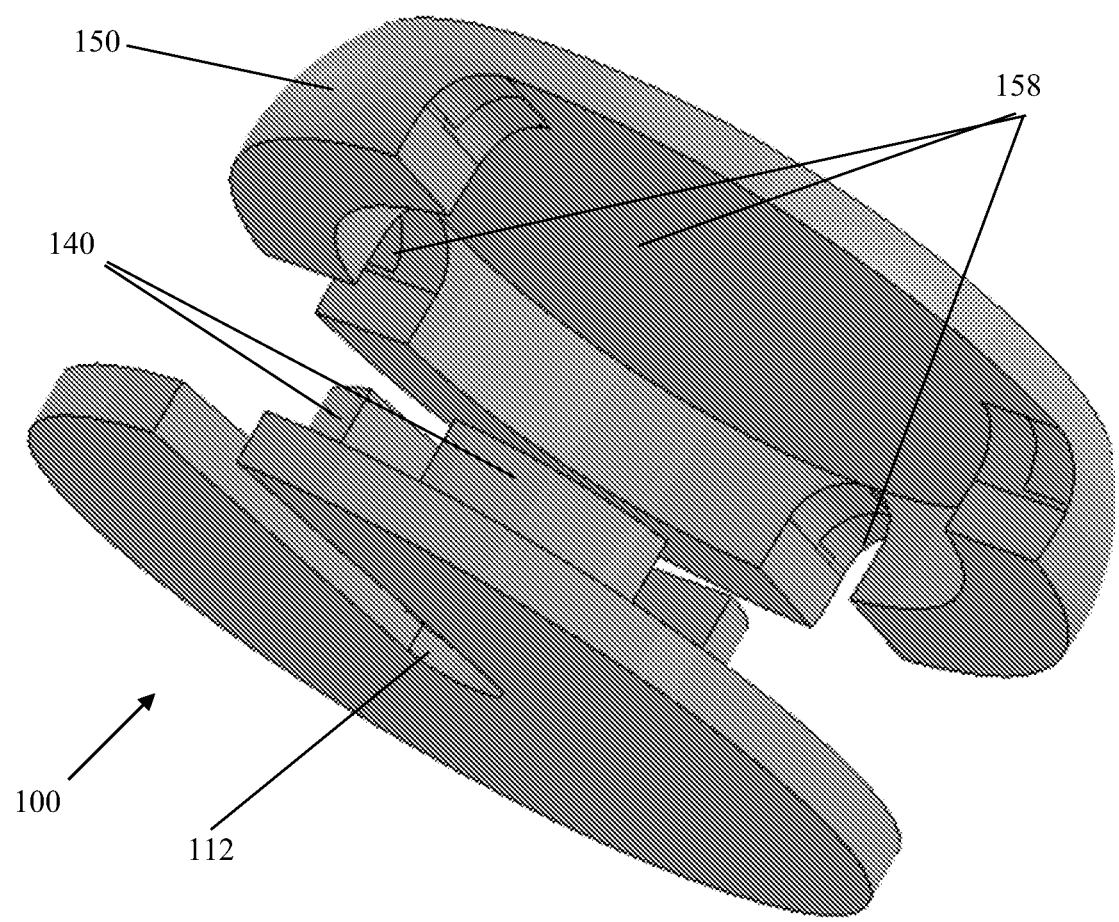
FIG. 29 is a bottom perspective view of the medical device anchor and cap suitable for use in practicing exemplary embodiments of the present disclosure.
Figure 30:
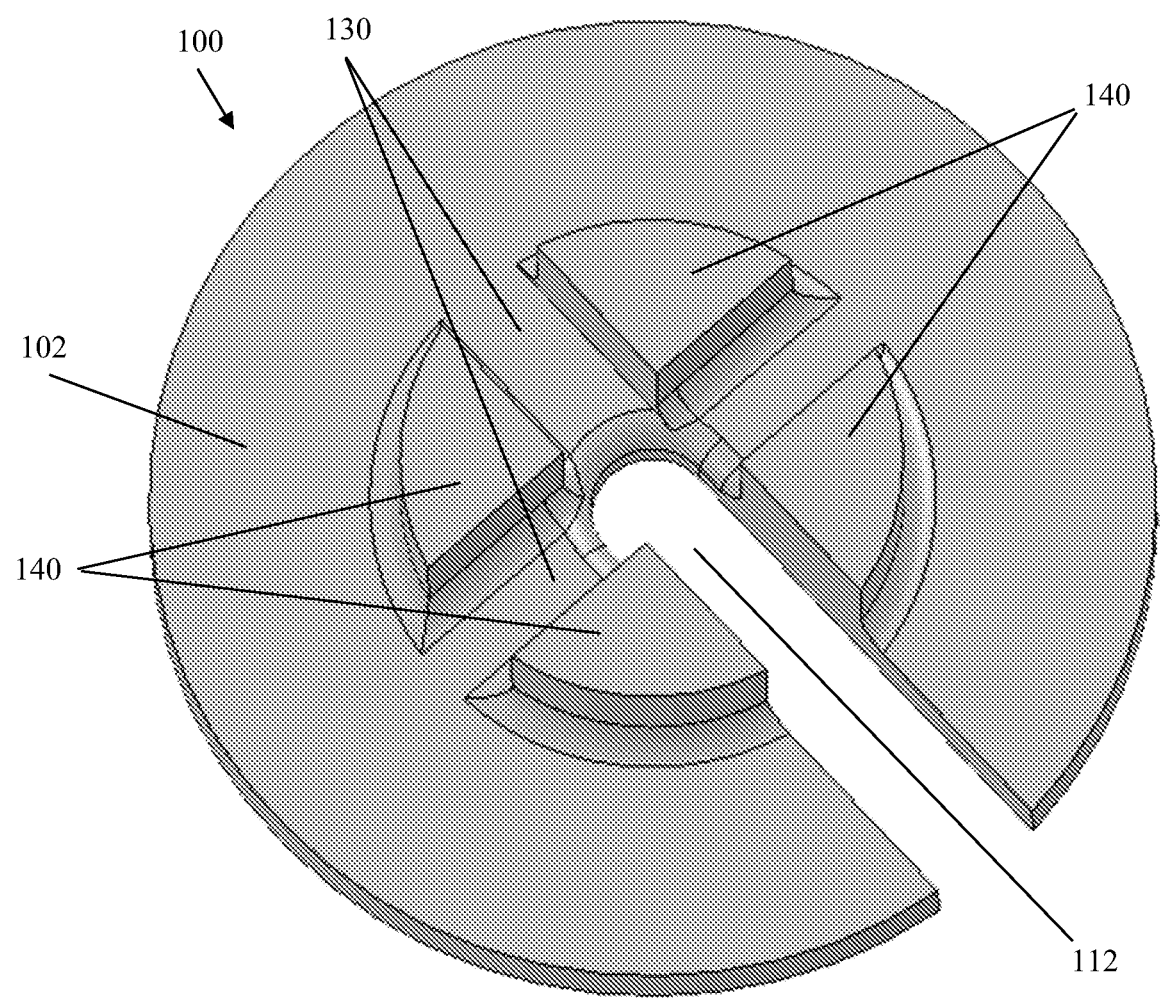
FIG. 30 is a top view of a medical device anchor suitable for use in practicing exemplary embodiments of the present disclosure.
Figure 31:
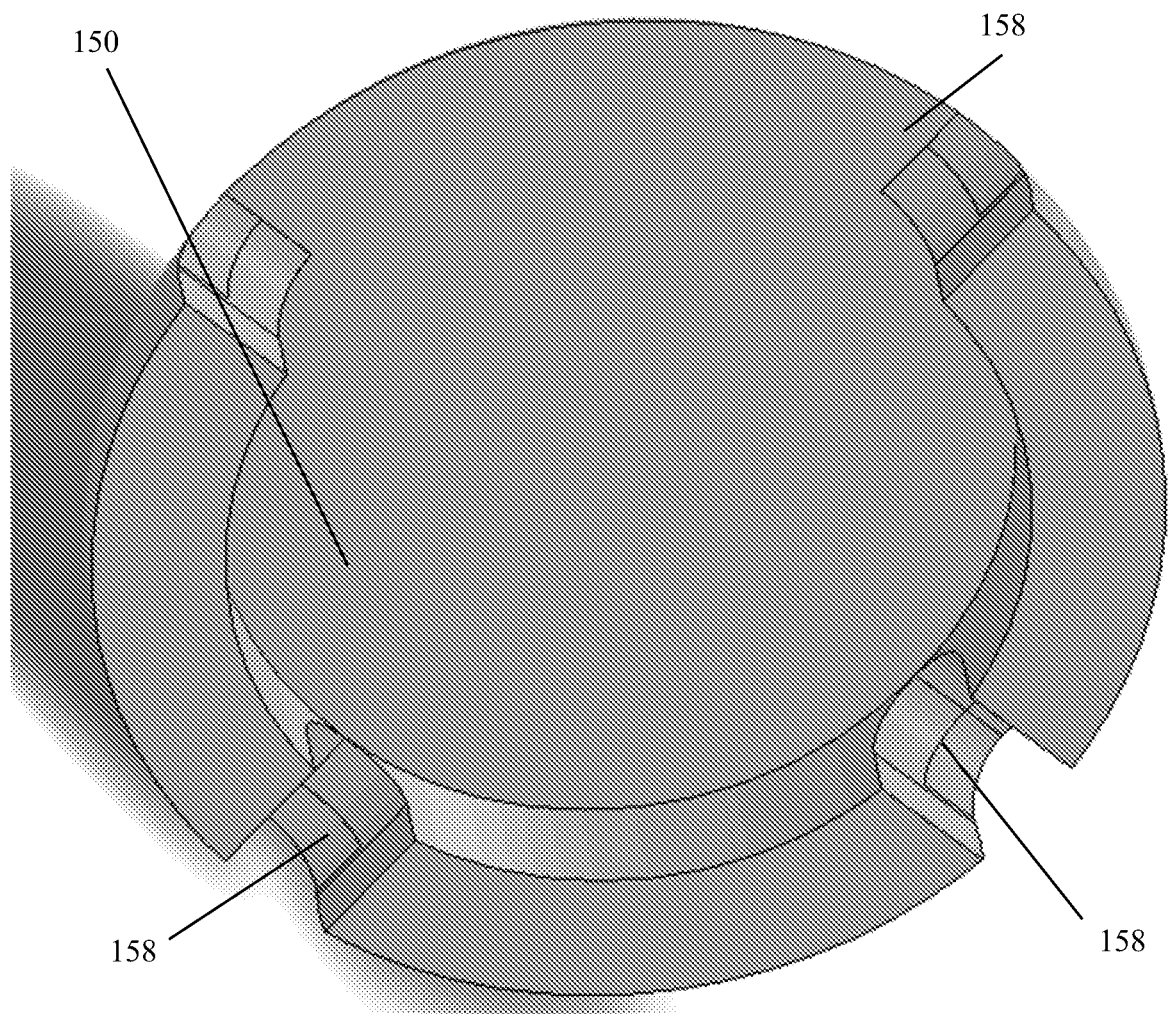
FIG. 31 is a bottom view of an exemplary cap suitable for use in practicing exemplary embodiments of the present disclosure.

Referring to FIGS. 22, 23, and 24, shown is a simplified embodiment of the embodiment depicted in FIG. 1. Shown in FIGS. 22, 23, and 24 are device anchor 100 having a hole 112. As depicted in FIGS. 22, 23, and 24, hole 112 does not extend from the edge portion 106 to the radial center of body 102. Rather hole 112 as depicted in FIGS. 22, 23, and 24 is located at the radial center circumscribed by body 102. Hole 112 provides a circular passageway from a top surface of body 102 to a bottom surface of body 102. Hole 112 is operably sized to allow a catheter or other medical device to pass through hole 112. Referring to FIGS. 26-31, depicted are another simplified embodiment of the embodiment depicted in FIG. 1. In this embodiment, device anchor 100 includes a body 102 and only four walls 140 located adjacent to hole 112. As depicted, hole 112 includes a space or gap that extends from a radial edge of body 102 to the radial center of body 102 between and adjacent to walls 140. Also depicted is cap 150 operable to removeably attach or affix to body 102. Cap 150 includes openings 158 located along the radial sides of cap 150 operable to accommodate a medical device such as a catheter.

Figure 8:
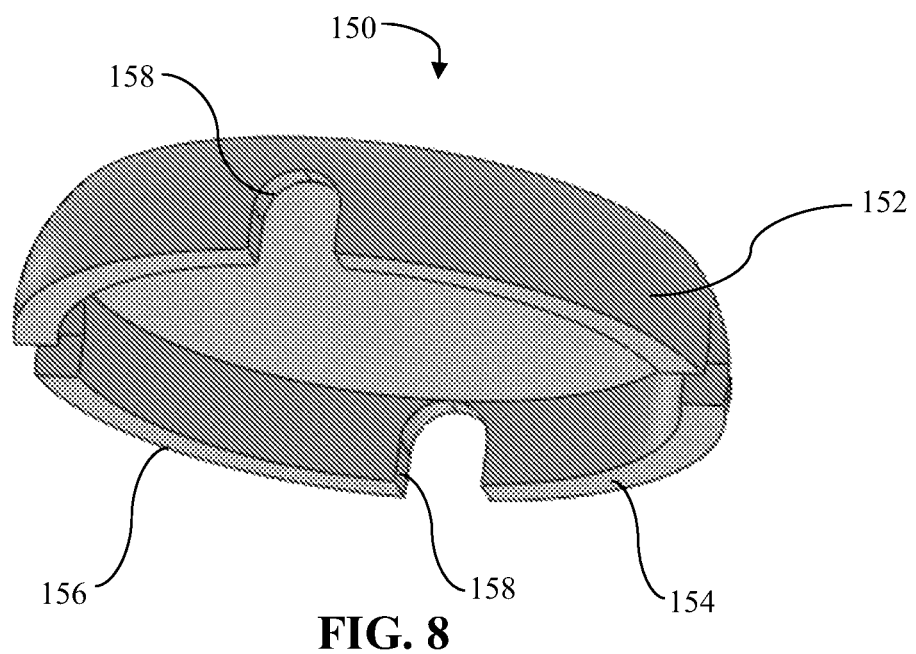
FIG. 8 is a side perspective view of a first embodiment of a cap for covering a medical device anchor of the present disclosure.
Figure 9:
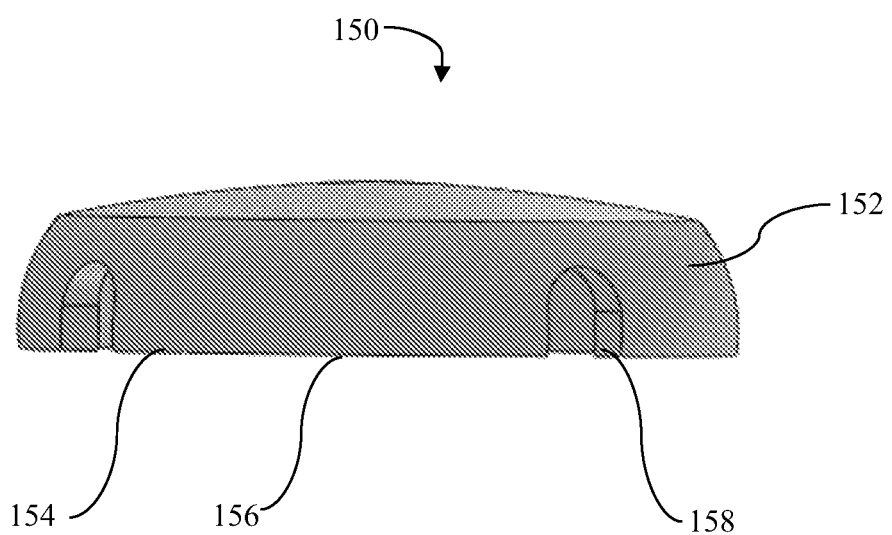
FIG. 9 is side elevational view of the cap of FIG. 8 of the present disclosure.
Figure 18:
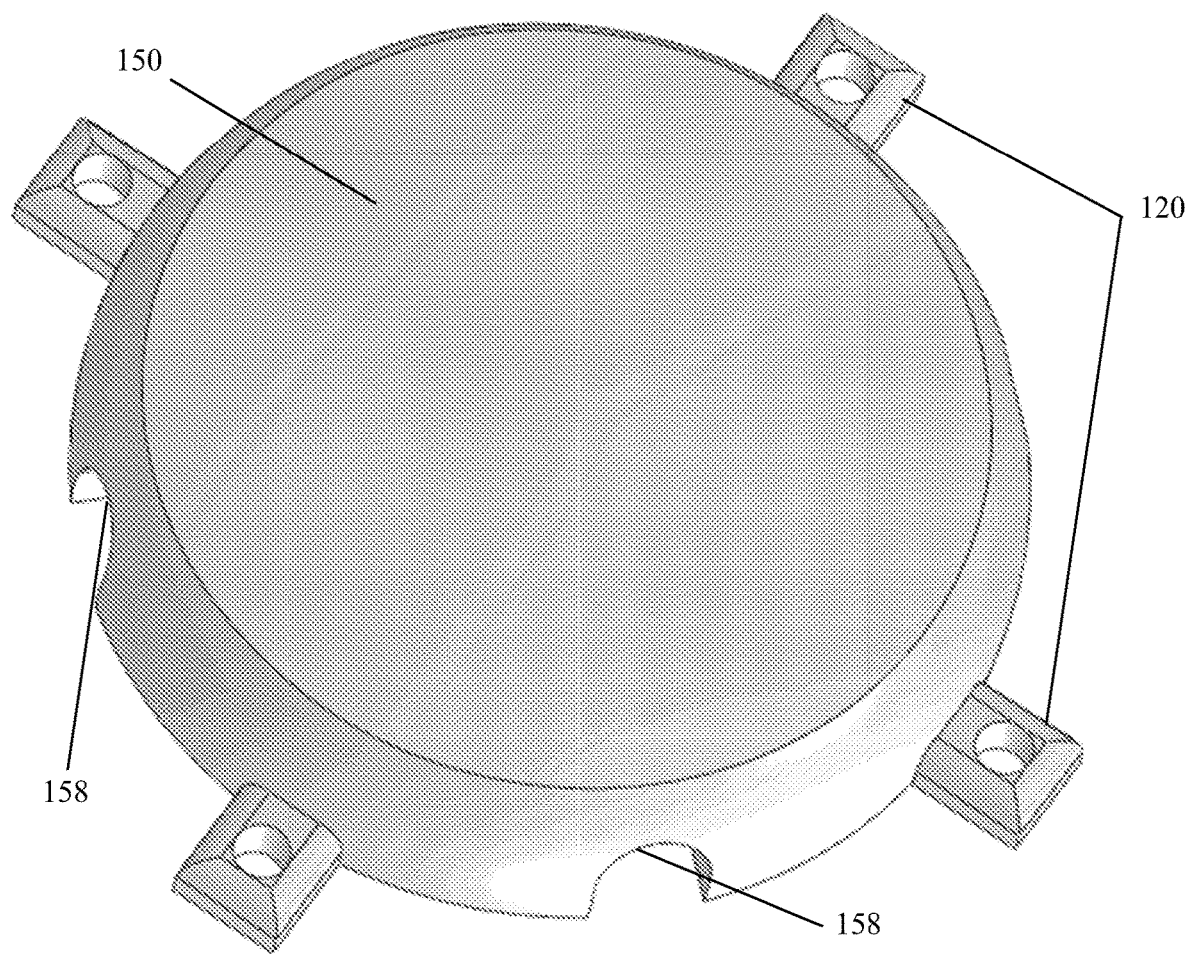
FIG. 18 is a top view of an exemplary cap suitable for use in practicing exemplary embodiments of the present disclosure.

Referring to FIGS. 8 and 9, shown are perspective views of a cap 150 for performing exemplary embodiments of this disclosure such as enclosing a top portion of the device anchor 100. The cap 150 includes a body 152, an edge 154, a lip 156 of the edge 154, and a plurality of openings 158. Embodiments of the present disclosure include the number of openings 158 to correspond to the number of terminal ends 132 of the plurality of channels 130 such that the medical device 160 may extend from the terminal end 132 of the channel 130 to the opening 158 of the cap 150. It should be appreciated that embodiments of cap 150 and device anchor 100 are operable to be removeably affixed to one another through the use of a friction fit, snap, clasp, latch, or other device operable to allow cap 150 and device anchor 100 to be removeably affixed to one another. Referring to FIG. 18, shown is a top view of an exemplary embodiment of cap 150. In this embodiment, cap 150 includes wings 120 extending radially outward from the sides of cap 150. Wings 120 provide holes that allow sutures/ties to hold the cap 150 and the device anchor 100 together and to a patient's skin.

Embodiments of the present disclosure include the cap 150 holding the medical device 160 within the channels 130 of the body 102 of the device anchor 100 so that the medical device 160 does not slip out when under load. The cap 150 also prevents tissue ingrowth. When implanted beneath the skin of a patient, tissue will be free to grow into and around the medical device that is being secured within the device anchor 100 if there is no cap present. This will make later disassembly more difficult. The cap 150 also minimizes potential patient tampering, assuring single use of the device anchor 100.

Further embodiments include the cap 150 having an array of openings 158 along its exterior that correspond to the size of the medical device 160 and the vertical location of the medical device 160 relative to the body 102 of the device anchor 100, allowing the medical device 100 to enter and exit accurately.

Alternatively, the cap 150 also may be formed without inlets or exits 158 along its exterior. In this embodiment, the body 102 of the device anchor 100 includes shortened notches along the exterior radius 106 of the body 102 that allows the medical device 160 to dip beneath the cap 150 at the entrance/exit point 116 of the device anchor 100. This embodiment allows for a simpler cap component manufacturing process.

Embodiments include the cap 150 further having exterior protrusions (not shown) to allow attachment of the cap 150 to the device anchor 100 or the patient with an elastomeric band, tie downs, twist ties, or any other method suitable for the intended purpose and understood by a person of ordinary skill in the art. The elastomeric band allows for securement to the patient similarly to a wristwatch or belt. The cap 150 also may further include exterior suture wings similar to the wings 120 (see FIG. 18) of the device anchor 100 for securement to tissue of the patient.

Further embodiments of the present disclosure include the cap 150 having a shallow dome shape on its exterior. The exterior curvature is critical for implanted devices, as prominent or sharp corners may cause tissue degradation.

Embodiments of the present disclosure include the cap 150 being secured to the body 102 of the device anchor 100 while maintaining a tamper proof seal to eliminate the potential for patient removal of the cap 150 and have access to the medical device 160. When removing the cap 150 from the body 102 of the device anchor 100, the cap 150 further limits the amount of pushing/pulling on the patient as the cap 150 is removed from the device anchor 100 and not directly from the soft tissue of the patient.

Alternatively, embodiments of the present disclosure include the cap 150 having the channels 130, the walls 140, and the inlets and outlets 116 incorporated into the underside of the cap 150 with the inlets and outlets 160 along the exterior edge 154 of the cap 150. In this embodiment, the cap 150 includes loops (not shown) along the exterior surface of the cap 150 to allow suturing or securing the cap 150 to the surrounding tissue of the patient. For example, the loops may secure the cap 150 against the skin or skull of the patient. Alternatively, the cap 150 may include an adhesive on the underside of the cap 150 along the lip 156 of the cap 150 to hold the cap 150 against the tissue of the patient.

Further embodiments of the present disclosure include the underside of the cap 150 having a surface or surfaces to secure the catheter 160 into the channels 130 with or without sutures. Examples of securing methods include: 1) threaded mating between the body 102 of the device anchor and the cap 150 including a "quarter-turn locking" mechanism; 2) a series of pillars (not shown) projecting from the underside of the cap 150 that correspond to a series of apertures in the body 102 of the device anchor 100 that are configured to be frictionally engaged, such as an interference fit (e.g., the cap 150 includes downward facing tapered pillars configured to interface with cylindrical holes in each of the central pegs/holes in the body 102 of the device anchor 100; with the medical device 160 in place, the protruding lid pillars are aligned with the body 102 holes and squeezed together with pressure or an additional tool for locking and unlocking); and 3) a clip mechanism on the underside of the cap 150 that secures the cap 150 to the device anchor 100, which when the center-top of the dome-shaped portion of the cap 150 is pressed down, the cap 150 deforms in a downward motion, thereby detaching the cap 150 from the device anchor 100 (an example of a flexible material capable of deforming includes flexion, which may be engaged to the edge portion 106 of the device anchor 100 and disengaged from the clips of the device anchor 100 to remove the cap 150 from the device anchor 100).

Figure 10:
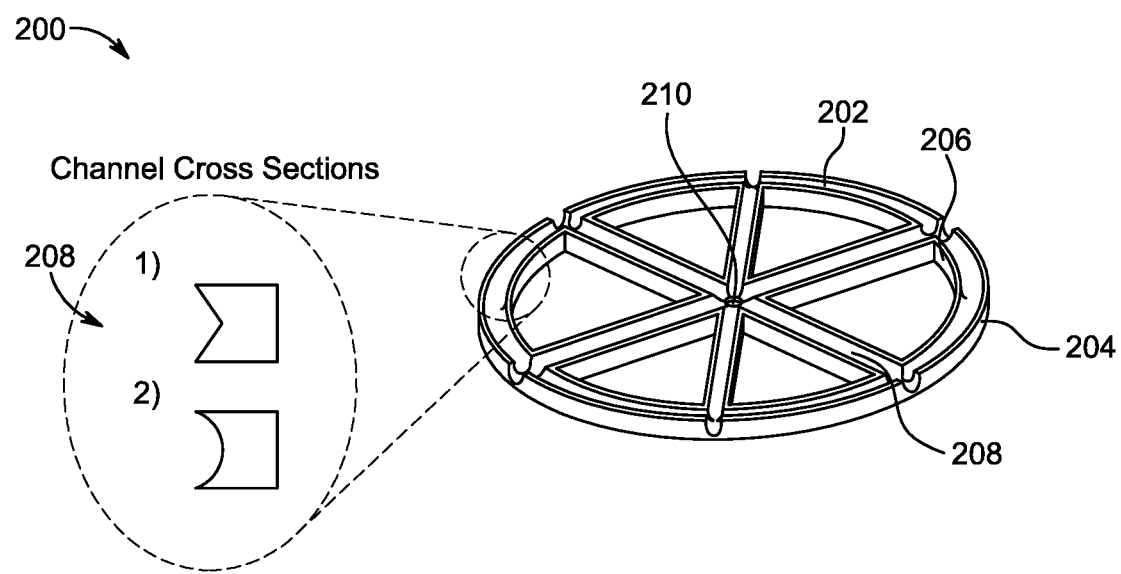
FIG. 10 is a top perspective view and a side cross-sectional view of a second embodiment of a medical device anchor of the present disclosure.

Referring to FIG. 10, shown is a perspective view of another exemplary medical device anchor operable for performing exemplary embodiments of the present disclosure. Shown in FIG. 10 is a device anchor 200 having a body 202, a plurality of channels 208, and a hole 210. Embodiments include the body 202 of the device anchor 200 having an outer portion 204 and an inner portion 206. Further embodiments include the outer portion 204 of the device anchor 200 having a channel configured to secure the medical device 160 to the device anchor 200.

Embodiments of the device anchor 200 include having six channels 208. However, embodiments of the present disclosure may include less or more channels 208 that are suitable for the intended purpose and understood by a person of ordinary skill in the art. Further embodiments include a method of securing medical devices 160 to the device anchor 200 by providing a device anchor 200 that is shaped similar to a wagon wheel or a car tire rim. The catheter 160 may enter either through the center "hub" 210 and pass through one of the "spokes" 208 to the exterior 204 of the device anchor 200 and pass about the rim 204 of the device anchor 200, or any combination of passing over the rim 204 of the device anchor 200 and through the spokes 208 for a horizontal application.

Embodiments of the present disclosure include the channels 208 of the device anchor 200 as having either a triangular cross-section or a circular cross-section. However, embodiments of the present disclosure include the channels 208 as having a polygonal-shaped cross-section that is suitable for the intended purpose and understood by a person of ordinary skill in the art.

Figure 11:
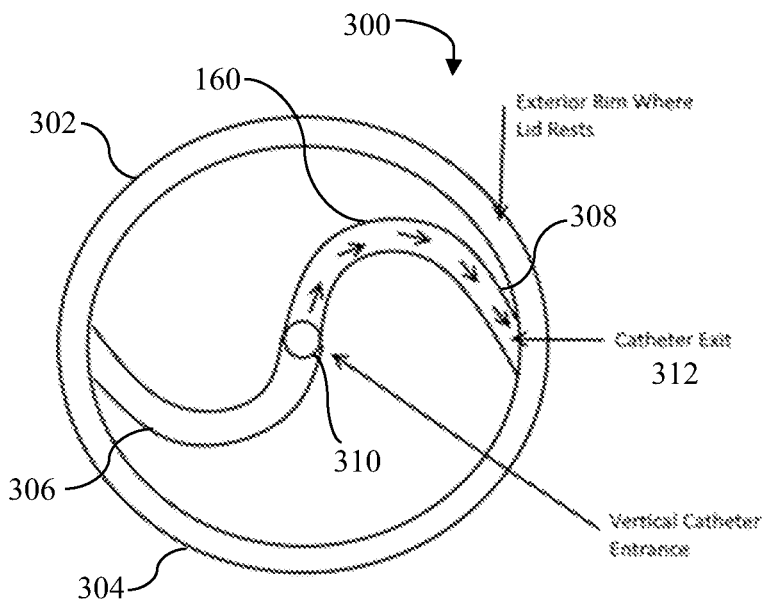
FIG. 11 is a top elevational view of a third embodiment of a medical device anchor of the present disclosure along with a first configuration of a medical device.
Figure 12:
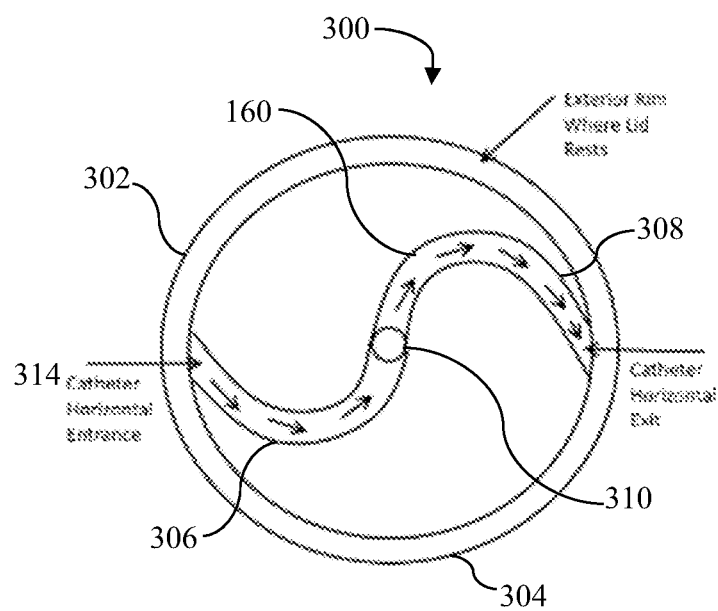
FIG. 12 is a top elevational view of the medical device anchor of FIG. 11 of the present disclosure along with a second configuration of a medical device.

Referring to FIGS. 11 and 12, shown are elevational views of another exemplary medical device anchor operable for performing exemplary embodiments of the present disclosure. Shown in FIGS. 11 and 12 is a device anchor 300 having a body 302, a channel 308, a hole 310, and an outlet 312. Embodiments of the present disclosure include the body 302 of the device anchor 300 as having an outer portion 304 and an inner portion 306. Embodiments include the medical device 160 entering the device anchor 300 from the hole 310, through the channel 308, and exiting through the outlet 312 of the device anchor 300. As shown in FIG. 12, embodiments of the present disclosure include the medical device 160 entering the device anchor from an inlet 314 and exiting through the outlet 312 of the device anchor 300.

Further embodiments of the present disclosure include wrapping the medical device 160 in a different shape in order to increase the surface friction force between the medical device 160 and the device anchor 300. The more surface-to-surface contact points there are, the greater the frictional force is applied to the medical device 160, which prevents repositioning of the medical device 160 within the device anchor 300. Wrapping the medical device 160 around a curved channel 308 as shown in FIG. 12 is one method. The curved channel 308 reduces the potential for occluding the lumen of a secured tubing 160, as there are no sharp "corners" (e.g., 90 degree bends) to pass over.

As shown in FIGS. 11 and 12, the medical device 160 is illustrated with two complex curved channels 308 facing opposite each other. As shown in FIG. 11, one curved channel 308 allows the catheter 160 to enter vertically through the hole 310, be folded over 90 degrees, and enter a single curved section of the channel 308. As shown in FIG. 12, two curved channels 308 allow the catheter 160 to enter horizontally and pass through the two opposing curved channels 308 to increase friction experienced by the catheter 160. Embodiments of the device anchor 300 may include two or more curved channels 308 to increase friction, thereby allowing the physician to have flexibility of the device anchor 300 usage.

Figure 13:
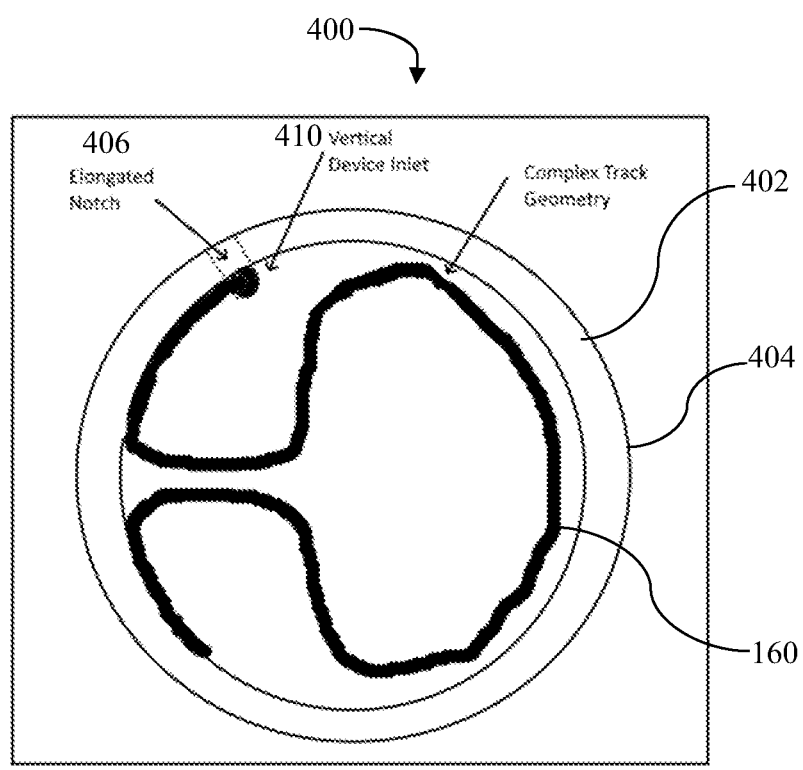
FIG. 13 is a top elevational view of a fourth embodiment of a medical device anchor of the present disclosure.
Figure 14:
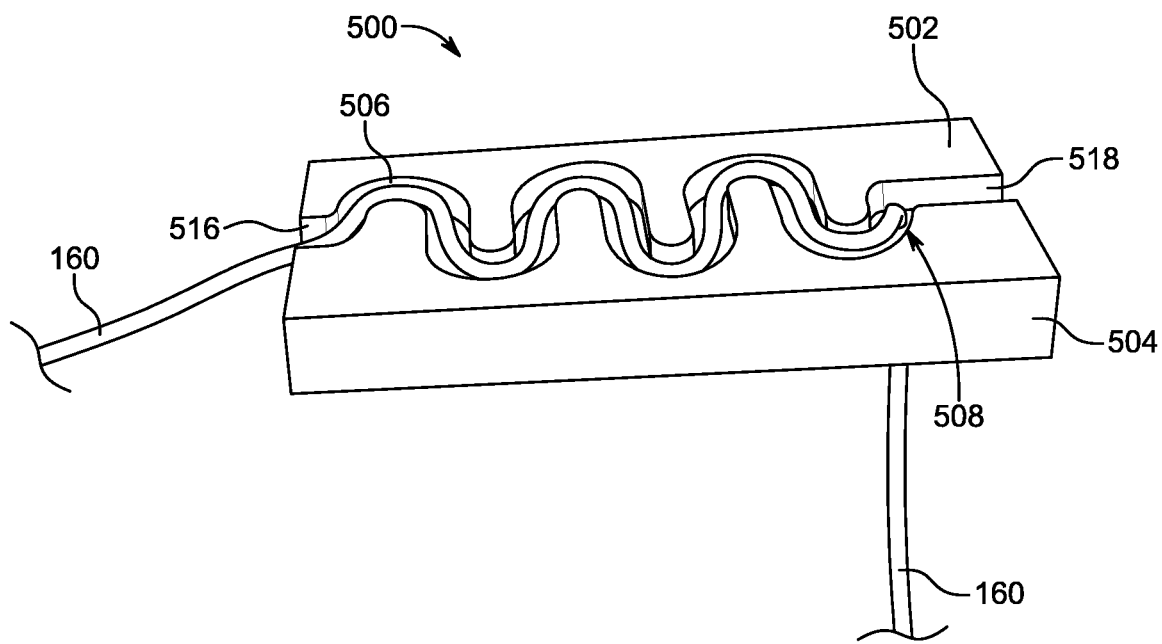
FIG. 14 is a side perspective view of a fifth embodiment of a medical device anchor of the present disclosure.

Referring to FIG. 13, shown is an elevational view of another exemplary medical device anchor operable for performing exemplary embodiments of the present disclosure. Shown in FIG. 13 is a device anchor 400 having a body 402 including an outer portion 404 and an inner portion 408. The outer portion 404 of the device anchor 400 includes a notch 406 to facilitate the medical device 160. The inner portion 408 of the device anchor 400 includes an inlet 410 for allowing the medical device 160 to enter the device anchor 400. The notch 406 and the inlet 410 are configured to allow the entry and the exit of the medical device 160 from the device anchor 400.

Embodiments of the present disclosure include a complex of curves that are incorporated into the circular shape of the device anchor 400. The entry into the body 402 of the device anchor 400 may be eccentric to the middle portion of the device anchor 400, while allowing the medical device 160 to pass through multiple curved channels. This applies an ample amount of pressure and friction that prevents the medical device 160 from slipping.

Further embodiments of the present disclosure include a wide variety of track/channel geometries that provide adequate curvature to the medical device 160 to provide sufficient friction and stop the medical device 160 from slipping within the device anchor 400.

Referring to FIGS. 14, 15, 17, 19, and 20, shown are perspective views of another exemplary medical device anchor operable for performing exemplary embodiments of the present disclosure. Shown in FIGS. 14, 15, 17, and 19 is a device anchor 500 having a body 502, a channel 506, and a hole 508. Embodiments include the body 502 of the device anchor 500 as having an outer perimeter 504, an inlet 516, and an outlet 518. Embodiments include the medical device 160 entering the device anchor 500 through the outer perimeter 504 of the body 502, winding through the channel 506, and exiting through the hole 508 out of a bottom portion 514 of the device anchor 500.

Embodiments of the present disclosure include the device anchor 500 having a linear-shaped body 502 with a "zig-zagging" channel 506 configured to secure the medical device 160 in the device anchor 500. The device anchor 500 takes advantage of the capstan principle of maximizing the angle of rotation that the medical device 160 travels, but in a linear configuration. Embodiments of the device anchor 500 include employing the device anchor 500 along the length of the medical device 160. Further embodiments of the device anchor 500 incorporate the ability to remove sections of the "zig-zag" in order to release more linear catheter 160 length for use. For example, the device anchor 500 may be a plurality of interconnected pieces forming a larger device anchor 500, but are removable from one another to form a smaller device anchor 500. Another example includes the medical device 160 being "half-way" removed from the channel 506 of the device anchor 500, thereby being partially secured in the device anchor 500. The zig-zag channel 506 also may include thinned sections 520 such that a physician may easily alter the length of the device anchor 506 after a segment of stored medical device 160 is removed. Zig-zag channel 506 includes one or more holes 522 located at the bottom of channel 560. Holes 522 provide a passageway for a catheter 160 or other device to pass from within channel 506 to the bottom of device anchor 500. It should be appreciated that holes 522 are spaced from one another along channel 506 such that there is at least one hole 522 located between thinned sections 520.

Further embodiments of the present disclosure include securing the medical device 160 within the linear complex of curved channels 500 with a lid/cap or with securing materials across the top portion of the device anchor 500 such as sutures, plates, screws of various materials, adhesives, or any other methods or materials suitable for the intended purpose and understood by a person of ordinary skill in the art.

Figure 15:
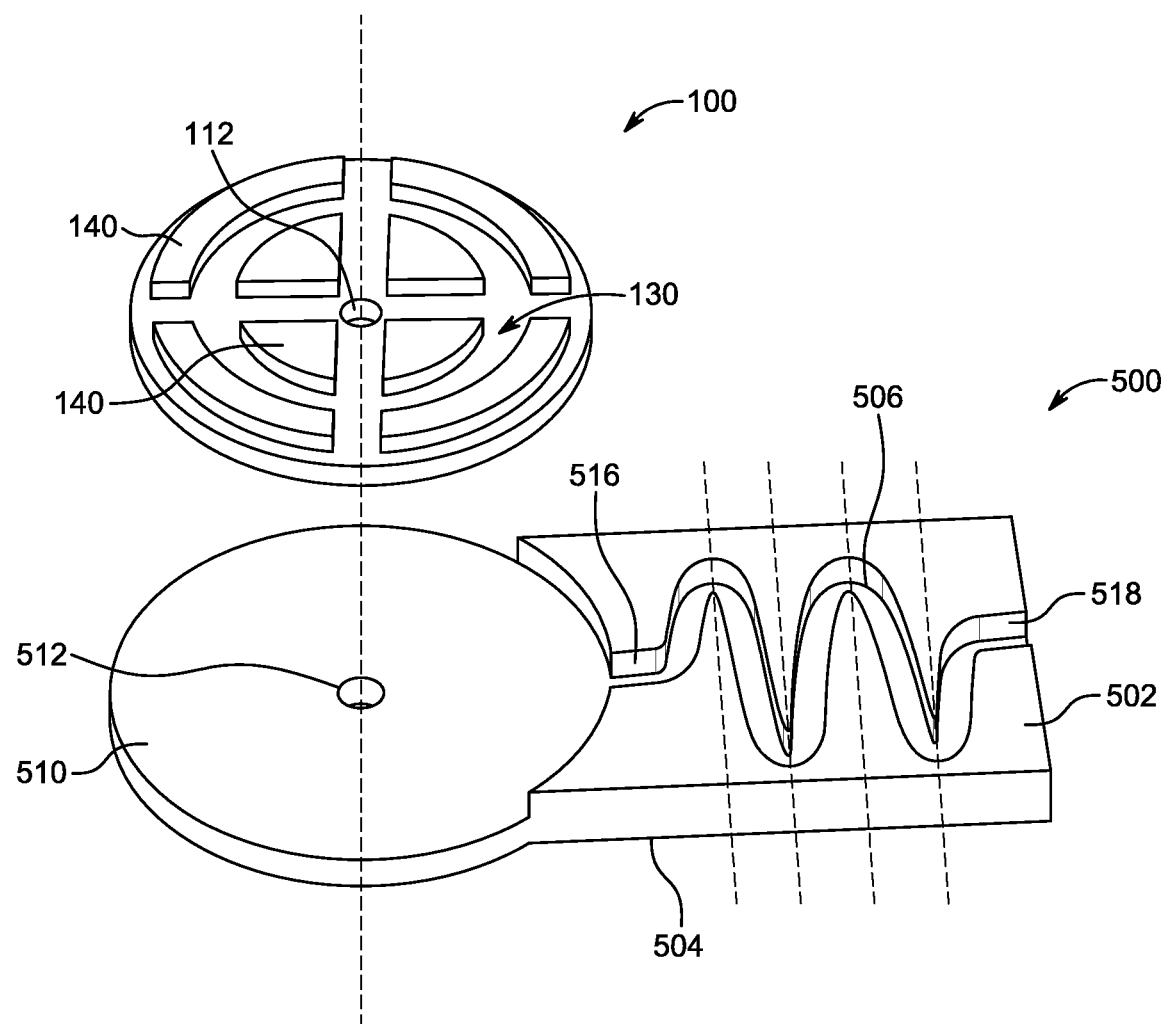
FIG. 15 is a side perspective view of the medical device anchor of FIG. 14 of the present disclosure along with an extended portion that accommodates the medical device anchor of FIG. 1 of the present disclosure.
Figure 17:
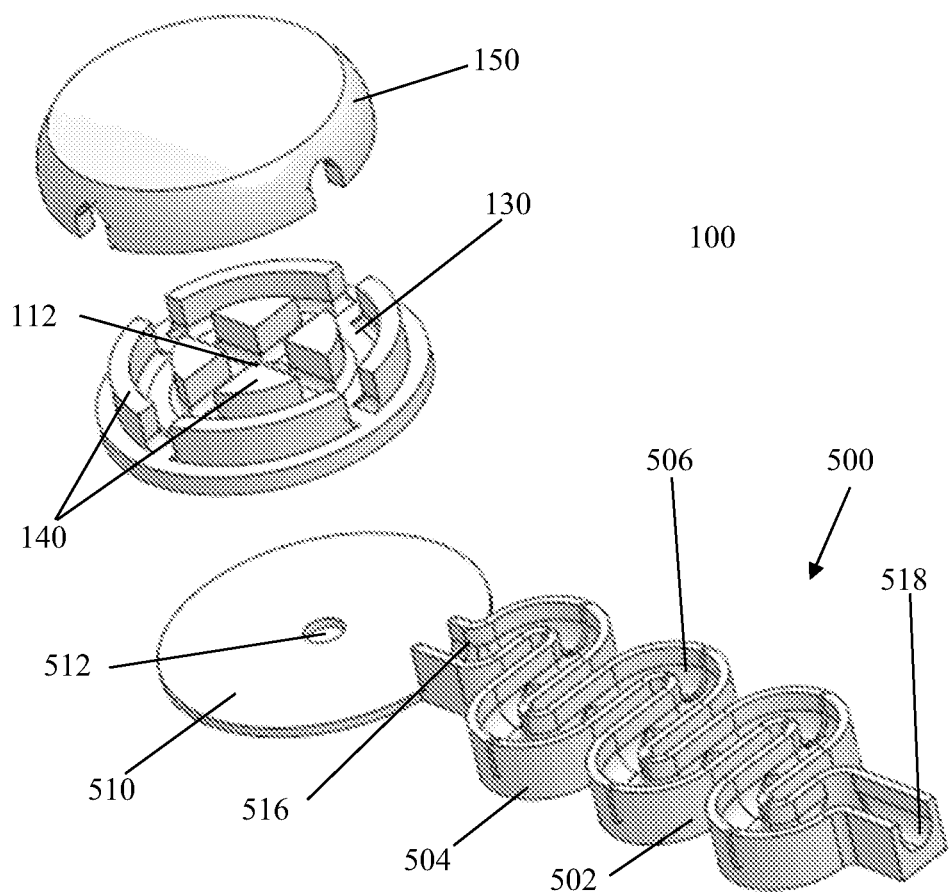
FIG. 17 is a top perspective view of an alternative embodiment of the medical device anchor suitable for use in practicing exemplary embodiments of the present disclosure.
Figure 19:
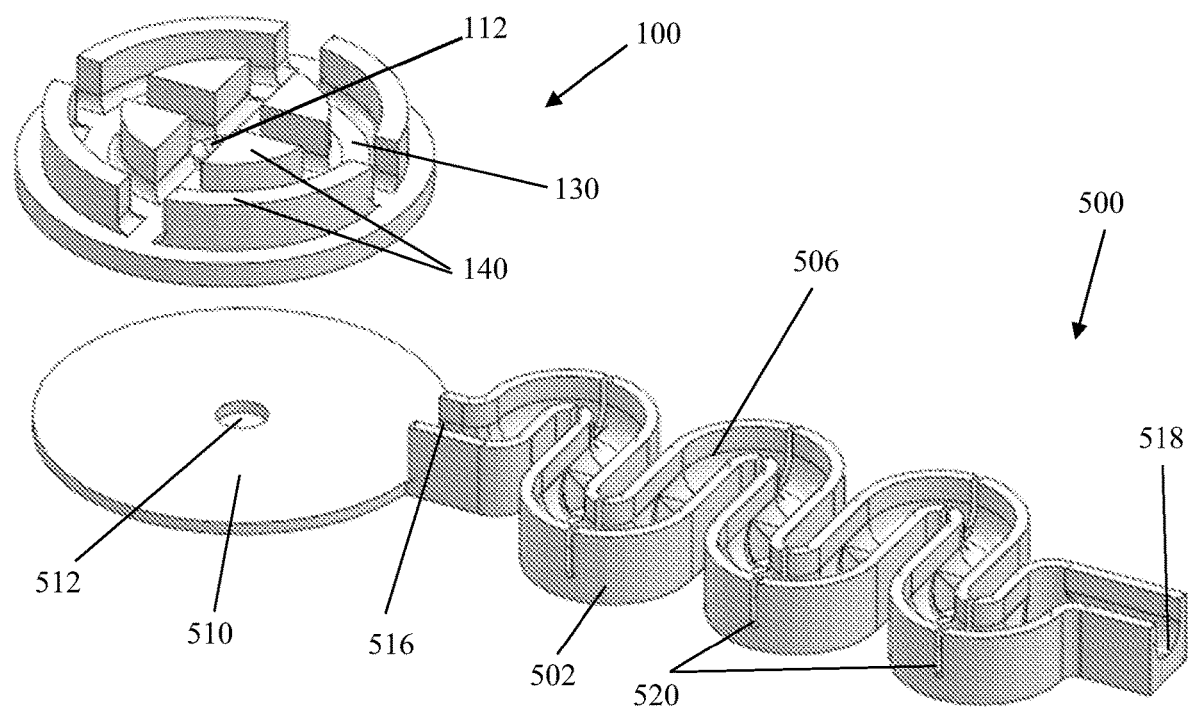
FIG. 19 is a side perspective view of an alternative embodiment of the medical device anchor suitable for use in practicing exemplary embodiments of the present disclosure.
Figure 20:
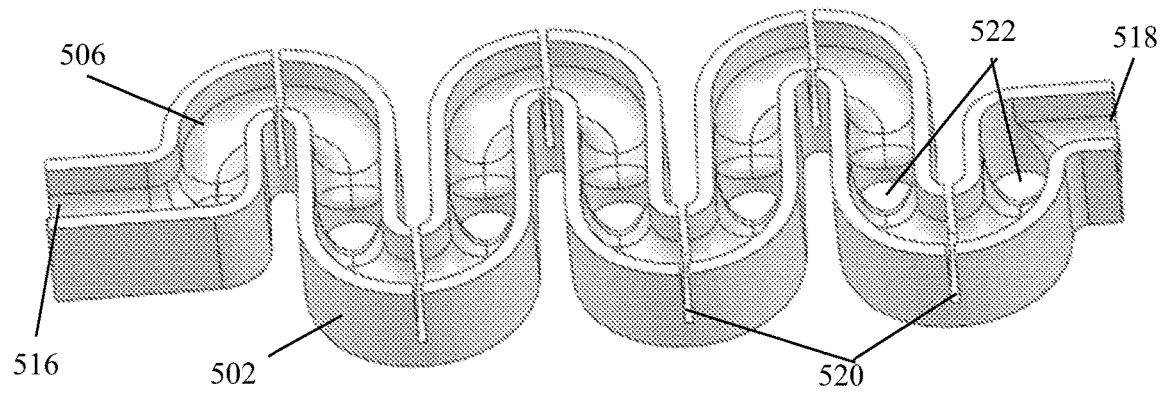
FIG. 20 is a side perspective view of a portion of an alternative embodiment of the medical device anchor suitable for use in practicing exemplary embodiments of the present disclosure.

As shown in FIGS. 15, 17 and 19, embodiments of the present disclosure include the device anchor 500 further having a platform 510 and a hole 512. Embodiments of the present disclosure include the platform 510 as having a similar surface area of the body 102 of the device anchor 100 to fully support the device anchor 100. Embodiments of the platform 510 of the device anchor 500 may also any shape suitable for the intended purpose and understood by a person of ordinary skill in the art. Embodiments include the hole 112 of the device anchor 100 being aligned with the hole 512 of the platform 510. Embodiments of the present disclosure include the device anchor 100 being attached or unattached to the platform 510 of the device anchor 500. If the device anchor 100 is secured to the platform 510 of the device anchor 500, the methods of securement may include adhesion, hook-and-loop, glue, epoxy, or any other type of securement suitable for the intended purpose and understood by a person of ordinary skill in the art.

Embodiments of the present disclosure include the device anchor 100 being configured to be rotatable about the platform 510 of the device anchor 500. The device anchor 100 may further be rotatable in 90 degree increments such that the outlet 116 of the body 102 of the device anchor 100 aligns with the inlet 516 of the device anchor 500.

Figure 21:
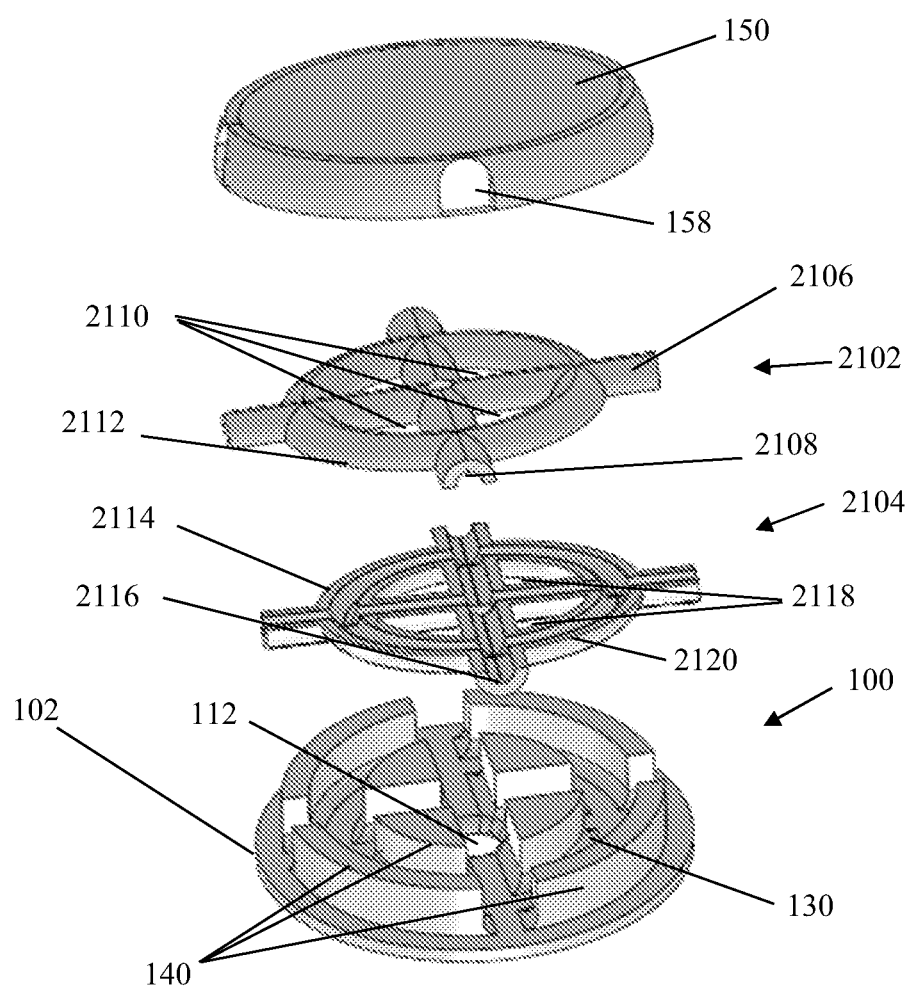
FIG. 21 is a top perspective view of another alternative embodiment of the medical device anchor suitable for use in practicing exemplary embodiments of the present disclosure.

Referring to FIG. 21, shown is another exemplary embodiment of device anchor 100. Shown in FIG. 21 is device anchor 100 having body 102, walls 140, and channels 130. Device anchor 100 also includes hole 112. Also shown in FIG. 21 is cap 150 having openings 158. FIG. 21 further depicts inserts 2102 and 2104. Inserts 2102 and 2104 are sized to be maintained within channels 130 of device anchor 100. Insert 2104 includes a body 2114 having curved channels 2116 sized to maintain a catheter or other similarly shaped device. Body 2114 defines spaces 2118 which provides a passageway from a top side of insert 2104 to a bottom side of insert 2104. Spaces 2118 correspond to walls 140 such that walls 140 can pass through spaces 2118. Insert 2104 includes a top confronting surface 2120 operable to contact confronting surface 2112 of insert 2102. Insert 2102 includes a body 2106 having curved channels 2108 sized to maintain a catheter or other similarly shaped device. Body 2106 defines spaces 2110 which provide a passageway from a top side of insert 2102 to a bottom side of insert 2102. Spaces 2110 correspond to spaces 2118. Embodiments provide that when confronting surfaces 2120 and 2112 are in contact with one another channels 2116 and 2108 are operable to maintain a location of a catheter such that the catheter maintained within channels 2116 and 2108 substantially restricts movement of the catheter. Cap 150 is operable to be located over at least a portion of inserts 2102 and 2104 such that inserts 2102 and 2104 can not move with respect to one another.

Figure 32:
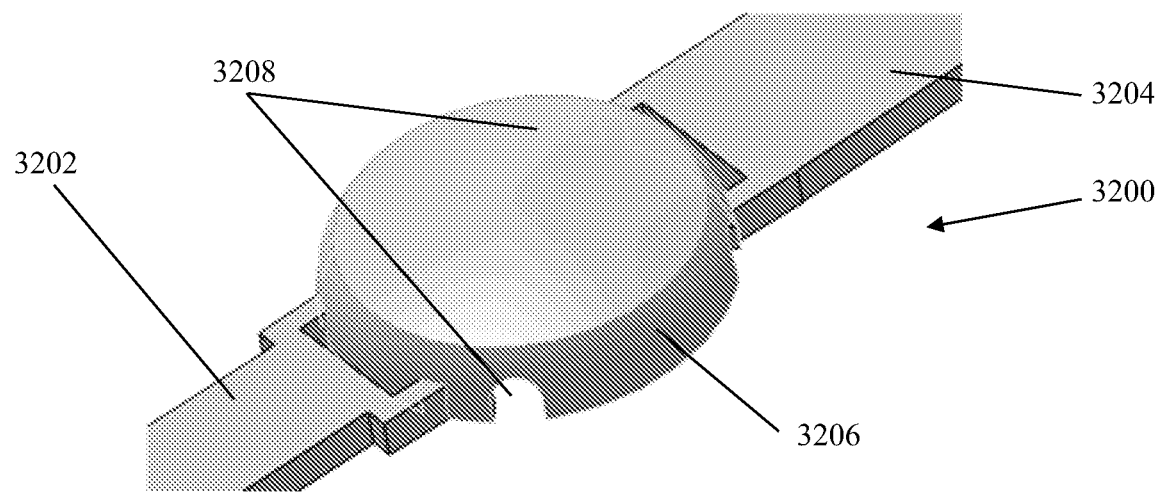
FIG. 32 is a close-up view of another alternative embodiment of a medical device anchor suitable for use in practicing exemplary embodiments of the present disclosure.
Figure 33:
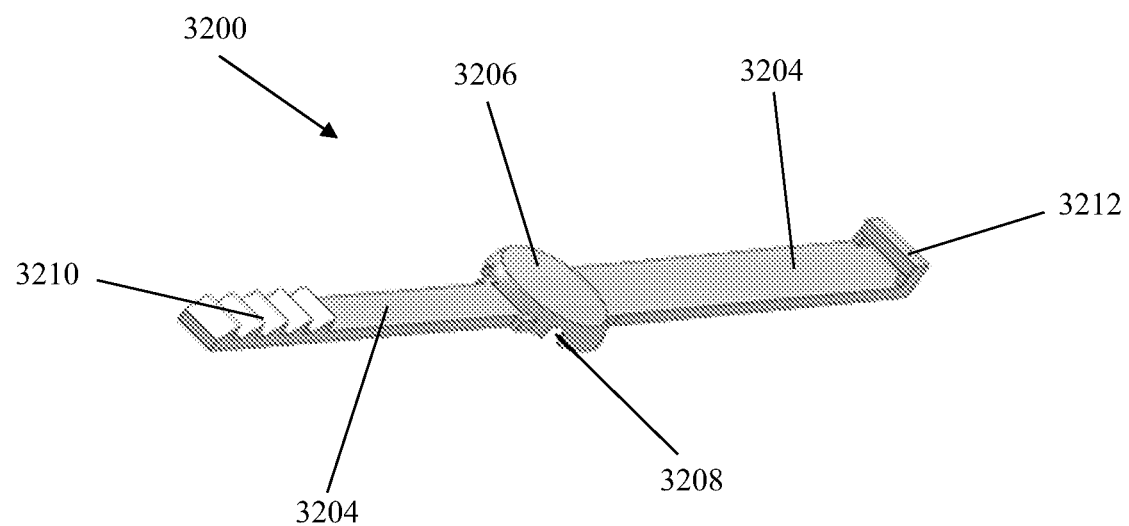
FIG. 33 is a perspective top view of another alternative embodiment of the medical device anchor suitable for use in practicing exemplary embodiments of the present disclosure.

Referring to FIGS. 32 and 33, depicted is yet another exemplary embodiment of a device 3200. Device 3200 includes two flexible bands 3202 moveably connected to a cap 3206. Cap 3206 includes a number of openings 3208 for accommodating a catheter. Flexible bands 3202 includes a connecting mechanism 3210, 3212 operable for removeably connecting the flexible bands 3202. Embodiments of connecting mechanism 3210, 3212 include any type of latch, buckle, Velcro, clasp, and the like operable to allow flexible bands to be removeably affixed or attached around a user's appendage. Embodiments of device 3200 are operable to be coupled to a device anchor 100 such that device anchor is removeably affixed to cap 3206. Device 3200 is then removeably affixed around a patient's wrist, arm, leg or other appendage such that connecting mechanism 3210, 3212 with flexible bands 3202 substantially prevents movement of device 3200 and device anchor 100 with respect to the patient.

The invention has been described in detail with particular reference to a presently preferred embodiment, but it will be understood that variations and modifications can be effected within the spirit and scope of the invention. The presently disclosed embodiments are therefore considered in all aspects to be illustrative and not restrictive. The scope of the invention is indicated by the appended claims, and all changes that come within the meaning and range of equivalents thereof are intended to be embraced therein.

The invention claimed is:

1. An apparatus for medical procedures, the apparatus comprising:
    a body having an inner portion and an edge portion, the edge portion defining a terminal end of the body, the body defining at least one surface spanning the inner portion and the edge portion, wherein the body is planar;
    a plurality of channels disposed on the at least one surface of the body, each channel of the plurality of channels having a first terminal end at the edge portion of the body, wherein the plurality of channels comprises at least one curve, wherein at least two channels of the plurality of channels intersect one another, wherein the body defines (i) a hole extending through the inner portion of the body, and (ii) a notch extending from the edge portion of the body to the hole, wherein each of the hole and the notch intersect at least one channel of the plurality of channels ; and
    a device anchor comprising an anchor body, the anchor body defining a channel having an inlet at a first end of the channel and an outlet at a second end of the channel, the anchor body comprising a plurality of paired thinned sections located along an outer perimeter of the channel, the anchor body comprising a platform defining a platform hole, wherein each one of the plurality of paired thinned sections define a space at a top portion of the channel, the channel comprising a plurality of holes located along a bottom of the channel, wherein each one of the plurality of holes is located between adjacent pairs of thinned sections, wherein the channel is zig-zag shaped.

2. The apparatus according to claim 1, the apparatus further comprising a plurality of walls, wherein the plurality of walls define spaces between the plurality of walls, and wherein the spaces define the plurality of channels.

3. The apparatus according to claim 1, the apparatus further comprising a cap having a cap body having a shape corresponding to the edge portion of the body, an edge of the cap body having a lip operable create a friction fit with the edge portion of the body.

4. The apparatus according to claim 3, wherein the cap comprises at least one opening, the opening located on the cap corresponding to a location of an intersection between at least one channel of the plurality of channels and the edge portion.

5. The apparatus according to claim 1, wherein the at least one of the plurality of channels is sized to operably maintain at least one tube.

6. The apparatus according to claim 5, wherein the tube is a catheter.

7. The apparatus according to claim 5, wherein the at least one curve is operable to maintain a location of the tube relative to the body.

8. The apparatus according to claim 1, wherein the plurality of channels are orthogonal to the hole.

9. A method of forming, the method comprising:
    (a) forming a body having an inner portion and an edge portion, the edge portion defining a terminal boundary of the body, the body defining at least one surface spanning the inner portion and the edge portion, wherein the body is planar;
    (b) forming a plurality of channels disposed on the at least one surface of the body, each channel of the plurality of channels having a first terminal end at the edge portion of the body, wherein the plurality of channels comprises at least one curve, wherein at least two channels of the plurality of channels intersect one another, wherein the body defines a hole extending through the inner portion of the body, wherein the hole intersects at least one channel of the plurality of channels; and
    (c) forming a device anchor comprising an anchor body, the anchor body defining a channel having an inlet at a first end of the channel and an outlet at a second end of the channel, the anchor body comprising a plurality of paired thinned sections located along an outer perimeter of the channel, wherein each one of the plurality of paired thinned sections define a space at a top portion of the channel, the channel comprising a plurality of holes located along a bottom of the channel, wherein each one of the plurality of holes is located between adjacent pairs of thinned sections, wherein the channel is zig-zag shaped.

10. The method according to claim 9, wherein the body defines a notch extending through the body, and wherein the notch intersects the at least one channel of the plurality of channels.

11. The method according to claim 9, wherein the body comprises a plurality of walls, wherein the plurality of walls define spaces between the plurality of walls, and wherein the spaces define the plurality of channels.

12. The method according to claim 9, the method further comprising forming a cap having a cap body having a shape corresponding to the edge portion of the body, an edge of the cap body having a lip operable create a friction fit with the edge portion of the body.

13. The method according to claim 9, wherein the at least one curve is operable to maintain a location of a tube relative to the body.

14. The method according to claim 9, wherein the plurality of channels are orthogonal to the hole.

15. An apparatus for medical procedures, the apparatus comprising:
    a device anchor comprising an anchor body, the anchor body defining a channel having an inlet at a first end of the channel and an outlet at a second end of the channel, the anchor body comprising a plurality of paired thinned sections located along an outer perimeter of the channel, wherein each one of the plurality of paired thinned sections define a space at a top portion of the channel, the channel comprising a plurality of holes located along a bottom of the channel, wherein each one of the plurality of holes is located between adjacent pairs of thinned sections, wherein the channel is zig-zag shaped.

* * * * *